(12) United States Patent
Alvaro et al.

(10) Patent No.: US 9,006,271 B2
(45) Date of Patent: Apr. 14, 2015

(54) 5-[5-[2-(3,5-BIS(TRIFLUOROMETHYL)-PHENYL)-2-METHYLPROPANOMETHYL-PROPANOYLMETHYLAMINO]-4-(4-FLUORO-2-METHYLPHENYL)]-2-PYRIDINYL-2-ALKYL-PROLINAMIDE AS NK1 RECEPTOR ANTAGONISTS

(71) Applicant: Nerre Therapeutics Limited, London (GB)

(72) Inventors: Giuseppe Alvaro, Verona (IT); Agostino Marasco, Verona (IT)

(73) Assignee: Nerre Therapeutics Limited, London (GB)

( * ) Notice: Subject to any disclaimer, the term of this patent is extended or adjusted under 35 U.S.C. 154(b) by 0 days.

(21) Appl. No.: 14/280,280

(22) Filed: May 16, 2014

(65) Prior Publication Data
US 2014/0249188 A1    Sep. 4, 2014

Related U.S. Application Data

(60) Continuation of application No. 13/681,925, filed on Nov. 20, 2012, now Pat. No. 8,822,504, which is a division of application No. 12/991,515, filed as application No. PCT/EP2009/055700 on May 12, 2009, now Pat. No. 8,344,005.

(30) Foreign Application Priority Data

May 14, 2008    (GB) .................................. 0808747.0

(51) Int. Cl.
*A61K 31/4439*    (2006.01)
*C07D 401/04*    (2006.01)

(52) U.S. Cl.
CPC .................................. *C07D 401/04* (2013.01)

(58) Field of Classification Search
USPC .......................................................... 514/343
See application file for complete search history.

(56) References Cited

FOREIGN PATENT DOCUMENTS

WO    02/08232    *    1/2002

* cited by examiner

*Primary Examiner* — Patricia L Morris
(74) *Attorney, Agent, or Firm* — Steinfl & Bruno, LLP

(57) ABSTRACT

The invention provides a compound of formula (I) or a pharmaceutically acceptable salt thereof, wherein R is $C_{1-4}$ alkyl

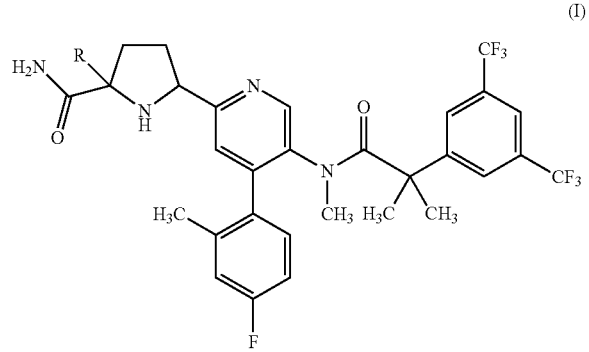

useful in the treatment of diseases and conditions for which antagonism of NK1 receptor is beneficial.

13 Claims, 1 Drawing Sheet

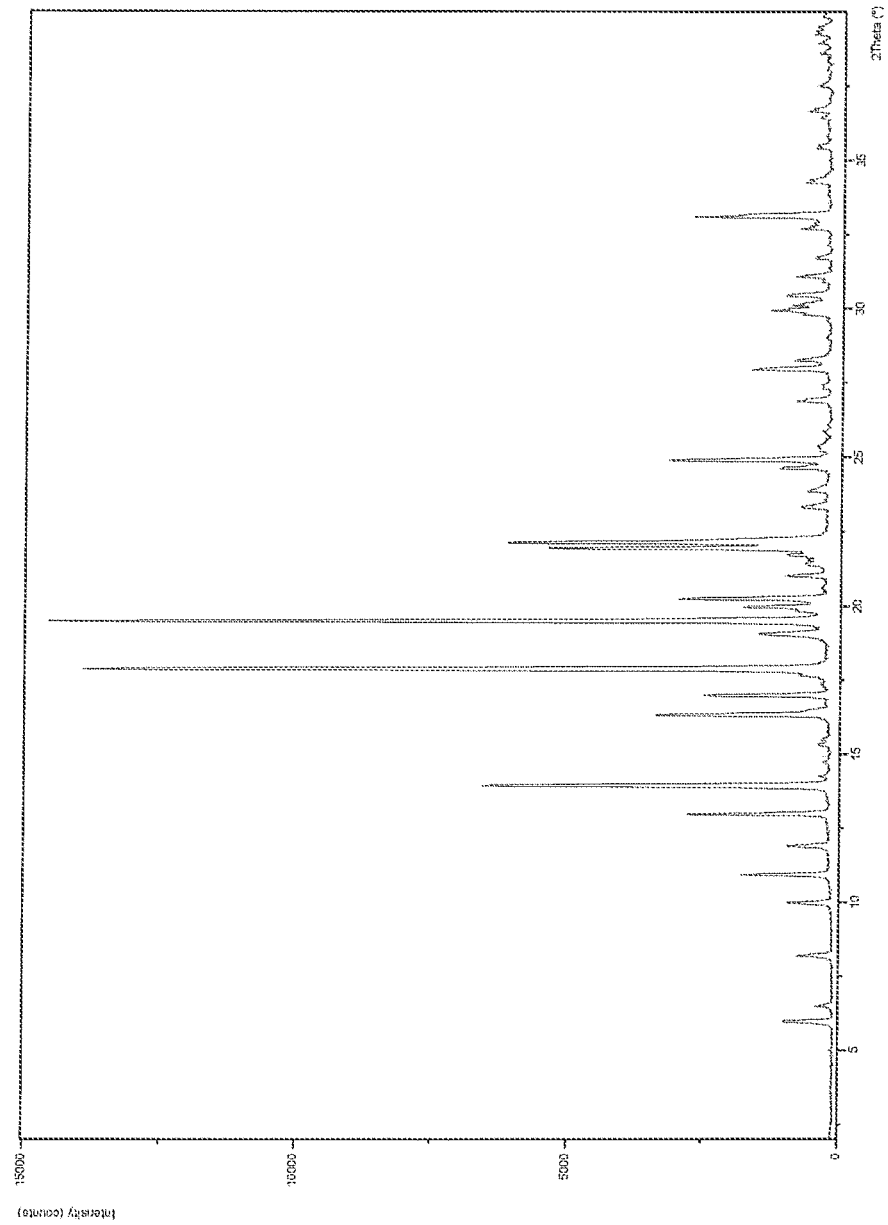

5-[5-[2-(3,5-BIS(TRIFLUOROMETHYL)-PHENYL)-2-METHYLPROPANOMETHYL-PROPANOYLMETHYLAMINO]-4-(4-FLUORO-2-METHYLPHENYL)]-2-PYRIDINYL-2-ALKYL-PROLINAMIDE AS NK1 RECEPTOR ANTAGONISTS

CROSS-REFERENCE TO RELATED APPLICATIONS

This application is a continuation application of U.S. patent application Ser. No. 13/681,925 filed on Nov. 20, 2012, now U.S. Pat. No. 8,822,504 which is incorporated by reference in its entirety and which, in turn, is a divisional application of U.S. Ser. No. 12/991,515, filed 5 Nov. 8, 2010, now U.S. Pat. No. 8,344,005, which was filed under 35 USC 371 as a United States National Phase Application of International Patent Application Serial Number PCT/EP2009/055700, filed May 12, 2009, which claims priority from United Kingdom application 0808747.0, filed May 14, 2008.

FIELD OF THE INVENTION

The present invention relates to novel prolinamide pyridine compounds having pharmacological activity, to processes for their preparation, to compositions containing them and to their medical uses.

BACKGROUND OF THE INVENTION

WO 2005/002577 (F. Hoffmann-La Roche AG), WO 2006/013050 (F. Hoffmann-La Roche AG) and WO 2007/028654 (SmithKline Beecham Corporation) describe series of pyridine derivatives which are claimed to be dual NK1/NK3 antagonists for treating schizophrenia. WO 02/16324 (F. Hoffmann-La Roche AG) describes 4-phenyl pyridine derivatives as NK1 receptor antagonists.

SUMMARY OF THE INVENTION

The present invention provides, in a first aspect, a compound of formula (I) or a pharmaceutically acceptable salt thereof,

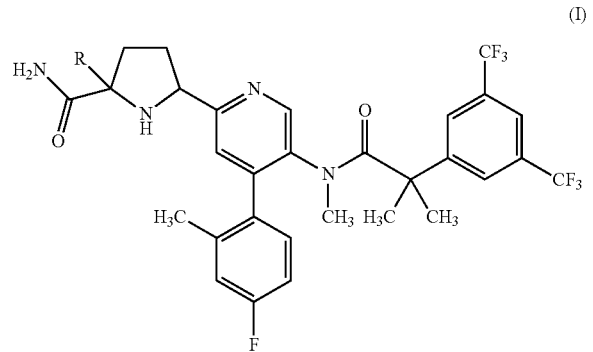

(I)

wherein R is $C_{1-4}$ alkyl.

BRIEF DESCRIPTION OF THE DRAWINGS

FIG. 1 is the XRPD pattern of the compound of Example 7. The XRPD pattern is expressed in terms of 2 theta angles and obtained with a diffractometer using copper Kα X-radiation.

Compounds of formula (I) may form acid addition salts with acids, such as conventional pharmaceutically acceptable acids, for example maleic, hydrochloric, hydrobromic, phosphoric, acetic, fumaric, salicylic, sulphate, citric, lactic, mandelic, tartaric, p-toluenesulfonic, benzoic and methanesulphonic.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Salts, solvates and hydrates of compounds of formula (I) therefore form an aspect of the invention.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a pharmaceutically acceptable anion or cation. Suitably pharmaceutically acceptable salts of the compound of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids. Salts having a non-pharmaceutically acceptable anion are within the scope of the invention as useful intermediates for the preparation of pharmaceutically acceptable salts and/or for use in non-therapeutic, for example, in vitro, situations.

The invention includes within its scope all possible stoichiometric and non-stoichiometric forms of the salts of the compounds of formula (I).

Compounds of formula (I) may be obtained as crystalline forms.

It is to be understood that these crystalline forms or a mixture thereof are encompassed within the scope of the invention.

Furthermore, some of the crystalline forms of the compounds of formula (I) may exist as polymorphs, which are included in the present invention.

Hereinafter, compounds of formula (I), their pharmaceutically acceptable salts, solvates, hydrates and crystalline forms thereof defined in any aspect of the invention (except intermediate compounds in chemical processes) are referred to as "the compounds of the invention".

The subject invention also includes isotopically-labelled compounds, which are identical to those recited in formula (I) but for the fact that one or more atoms are replaced by an atom having an atomic mass or mass number different from the atomic mass or mass number usually found in nature. Examples of isotopes that can be incorporated into compounds of the invention or pharmaceutically acceptable salts thereof include isotopes of hydrogen, carbon, nitrogen, oxygen, phosphorous, sulphur, fluorine, iodine, and chlorine, such as $^2H$, $^3H$, $^{11}O$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the invention that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

Isotopically labelled compounds of the invention can generally be prepared by carrying out the procedures disclosed in the Schemes and/or in the Examples below, by substituting a readily available isotopically labelled reagent for a non-isotopically labelled reagent It will be appreciated by those skilled in the art that compounds of formula (I) contain two asymmetric carbon atoms (namely the carbon atom shown as * in the formulae from (Ia) to (Id).

(Ia)

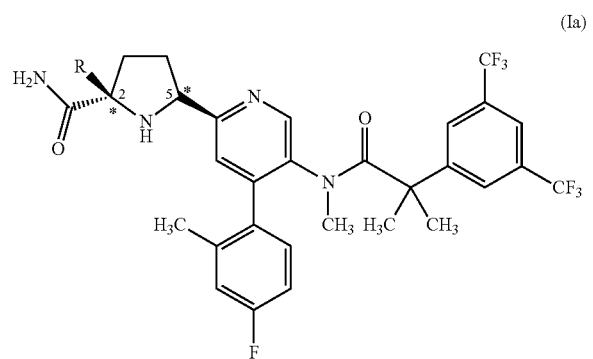

(Ib)

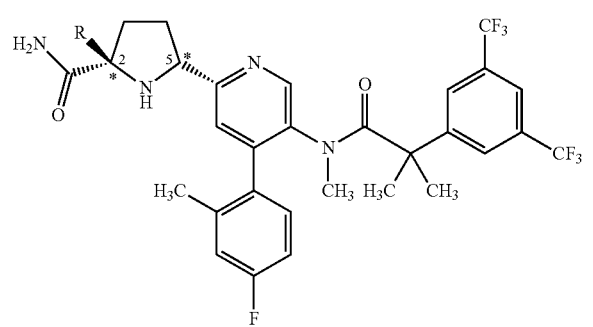

(Ic)

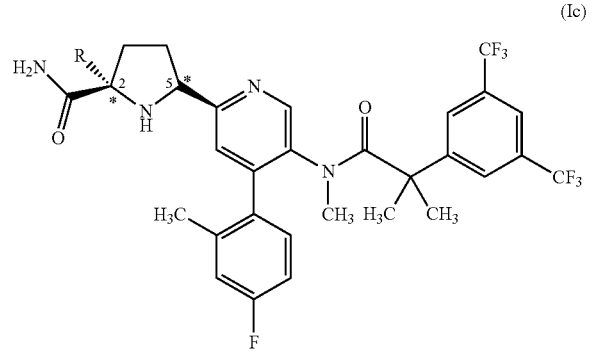

(Id)

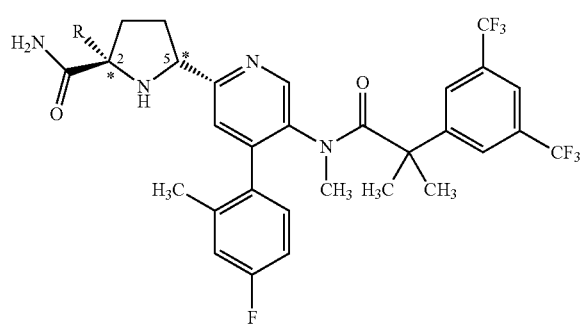

The wedge shaped bond indicates that the bond is above the plane of the paper and it is referred to as β configuration. The broken bond indicates that the bond is below the plane of the paper and is in the α configuration.

The configuration at the carbon 5 of the pyrrolidine ring is S for compounds (Ia) and (Ic) and R for compounds (Ib) and (Id).

The assignment of the R or S configuration has been made according to the rules of Cahn, Ingold and Prelog, Experientia 1956, 12, 81.

It will be understood that the invention encompasses all the above diastereoisomers or enantiomers of the compound of formula (I) and the mixture thereof including racemates and the reference to a compound of formula (I) includes all said stereoisomeric forms unless otherwise stated.

In one embodiment of the invention R is methyl.

In a further embodiment, the compound of the invention is selected from a list consisting of:

(5R)-5-[5-[{2-[3,5-bis(trifluoromethyl)phenyl]-2-methyl-propanoyl}(methyl)amino]-4-(4-fluoro-2-methylphenyl)-2-pyridinyl]-2-methyl-D-prolinamide (Ie);

(Ie)

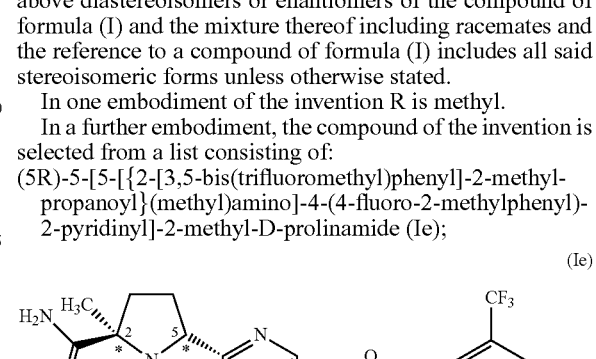

(5R)-5-[5-[{2-[3,5-bis(trifluoromethyl)phenyl]-2-methyl-propanoyl}(methyl)amino]-4-(4-fluoro-2-methylphenyl)-2-pyridinyl]-2-methyl-L-prolinamide (If);

(If)

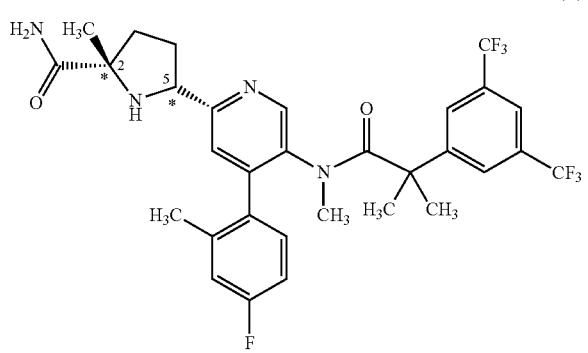

(5S)-5-[5-[{2-[3,5-bis(trifluoromethyl)phenyl]-2-methyl-propanoyl}(methyl)amino]-4-(4-fluoro-2-methylphenyl)-2-pyridinyl]-2-methyl-D-prolinamide (Ig);

(Ig)

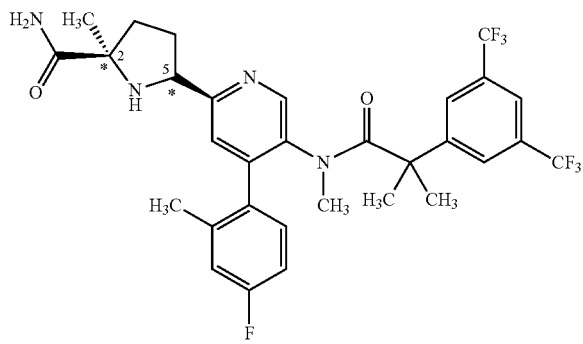

or a pharmaceutically acceptable salt of (Ie), (If) or (Ig).

In a further embodiment, the compound of the invention is (5R)-5-[5-[{2-[3,5-bis(trifluoromethyl)phenyl]-2-methyl-propanoyl}(methyl)amino]-4-(4-fluoro-2-methylphenyl)-2-pyridinyl]-2-methyl-D-prolinamide (Ie) or a pharmaceutically acceptable salt thereof.

In a further embodiment, the compound of the invention is (5R)-5-[5-[{2-[3,5-bis(trifluoromethyl)phenyl]-2-methyl-propanoyl}(methyl)amino]-4-(4-fluoro-2-methylphenyl)-2-pyridinyl]-2-methyl-D-prolinamide (Ie).

In a yet further embodiment, the compound of the invention is hydrochloride salt of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Ie).

In a yet further embodiment, the compound of the invention is bis-hydrochloride salt of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Ie).

In a yet further embodiment, the compound of the invention is tartrate salt of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Ie).

In a further embodiment the compound of the invention is benzoate salt of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Ie).

In a further embodiment the compound of the invention is fumarate salt of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Ie).

In a further embodiment the compound of the invention is citrate salt of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Ie).

The present invention also provides a process for the preparation of the compound of formula (I) or a pharmaceutically acceptable salt thereof, which process comprises: reacting the compound of formula (H), wherein R is $C_{1-4}$ alkyl, (II)

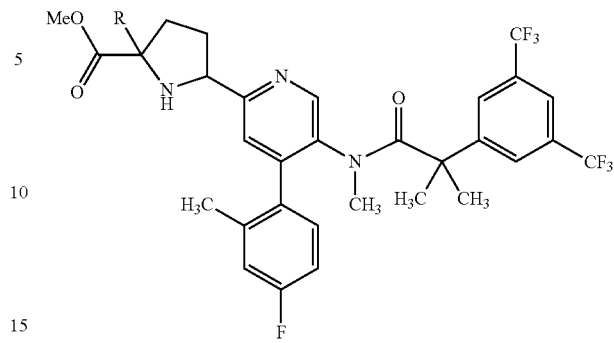

with ammonia in a suitable solvent such as methanol at suitable temperature such as 20-70° C., optionally thereafter followed by conversion to a pharmaceutically acceptable salt.

In a further embodiment, compounds of the invention can be prepared by a process which comprises the reduction of a compound of formula (III), (III)

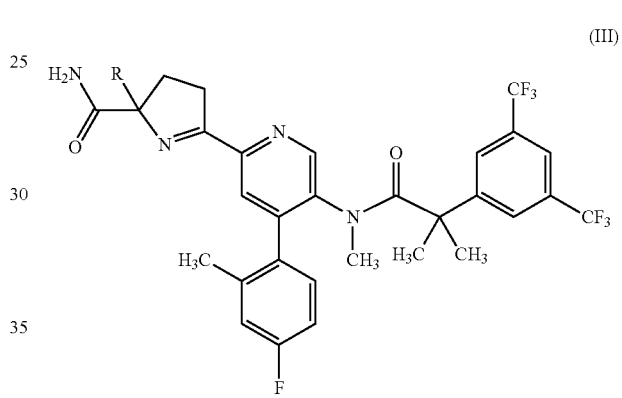

wherein R $C_{1-4}$ alkyl, using a suitable reducing agent, such as $NaBH_4$ in a suitable solvent, such as THF, or methanol at a suitable temperature ranging from 0° C. to room temperature or with borane tetrahydrofuran complex solution in a suitable solvent such as THF at a temperature ranging from −78° C. to r.t. or with sodium cyanoborohydride or triacetoxy borohydride in the presence of trifluoroacetic acid in a suitable solvent such as dichloromethane at a suitable temperature such as r.t., optionally thereafter followed by conversion to a pharmaceutically acceptable salt.

The compound of formula (II) may be prepared by alkylation of a compound of formula (IV), (IV)

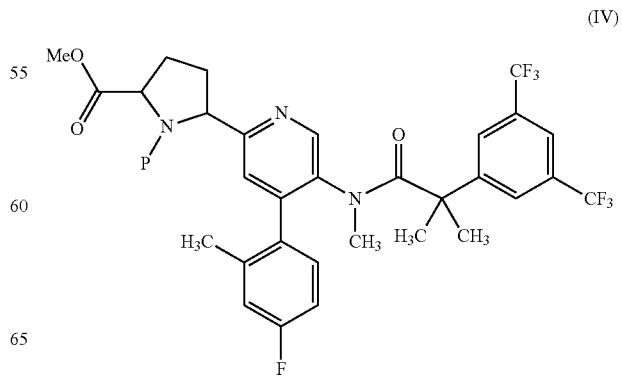

wherein P is a suitable protecting group, followed by the removal of the protecting group P. Alkylation reaction typically comprises reacting a compound of formula (IV) with a suitable base such as lithium bis(trimethylsilyl)amide in a suitable solvent such as THF at a suitable temperature ranging from −78° C. to room temperature for a time ranging from few minutes to hours, followed by in situ addition of a suitable electrophile R—X wherein R is $C_{1-4}$ alkyl and X is a suitable leaving group such as halogen (i.e. iodo), mesyl, tosyl, trifluoromethanesulfonyl at a suitable temperature ranging from −78° C. to high temperature.

The removal of protecting group p can be carried out using the well known proceedings for removal of N protecting group.

Thus, for example, when P represents Boc, said deprotection reaction can be carried out with trifluoroacetic acid in a suitable solvent such as dichloromethane at a suitable temperature such as room temperature.

In a further embodiment of the invention compounds of formula (II) or (IV) may be prepared by reduction of an imine compound of formula (V),

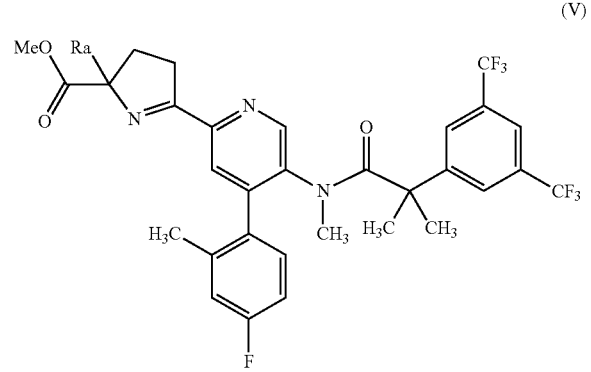

(V)

wherein Ra is hydrogen or $C_{1-4}$ alkyl, using a suitable reducing agent, such as NaBH$_4$, in a suitable solvent, such as THF or methanol at a suitable temperature ranging from 0° C. to room temperature or with borane tetrahydrofuran complex solution in a suitable solvent such as THF at a temperature ranging from −78° C. to r.t. or with sodium cyanoborohydride in the presence of aq. NH$_4$Cl saturated solution in a suitable solvent such as acetonitrile at a suitable temperature such as r.t., optionally followed by protection of the amine N with protecting group P.

In a further embodiment of the invention compounds of formula (II) or (IV) may be obtained by a reaction of a compound of formula (VI), wherein Ra is hydrogen or $C_{1-4}$ alkyl,

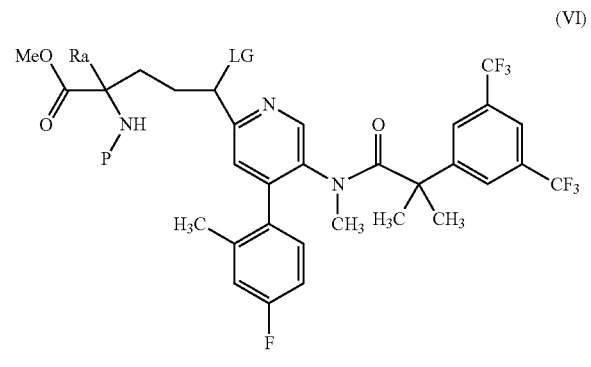

(VI)

LG is a suitable leaving group such as mesilate or tosilate and P is a suitable nitrogen protecting group such as tertbutyloxycarbonyl (Boc), which comprises deprotection of the nitrogen protecting group P, followed by in situ cyclisation reaction of the resulting deprotected intermediate to form the proline derivative optionally followed by protection of the amine N with protecting group P to obtain (II) or (IV).

Thus, for example, when P represents Boc said deprotection reaction may typically comprise reacting a compound of formula (VI) with a mixture of dichloromethane and trifluoroacetic acid. In situ cyclisation may be carried out during work-up by using aqueous sodium carbonate at room temperature.

The compound of formula (V) may be prepared by reaction of a compound of formula (VII),

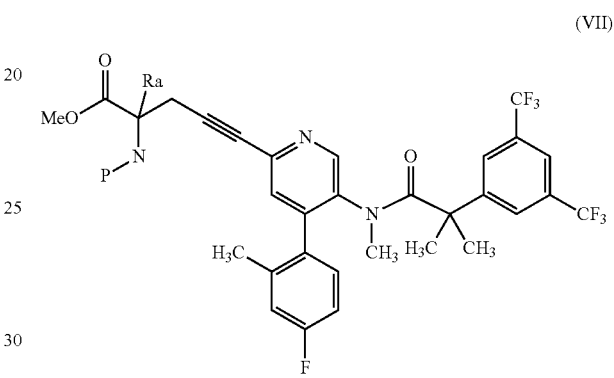

(VII)

wherein Ra is hydrogen or $C_{1-4}$ alkyl, P is a suitable nitrogen protecting group such as tertbutyloxycarbonyl (Boc), which comprises deprotection of nitrogen protecting group P, followed by a metal-catalyzed in situ intramolecular cyclisation of the resulting free amino ester to form the compound (V).

For example, when P represents Boc, said deprotection reaction may typically comprise reacting a compound of formula (V) with trifluoroacetic acid in dichloromethane. The deprotected intermediate may then be cyclized using a suitable metal catalyst such as Ag(I)-catalyst e.g AgOTf in a suitable solvent, such as acetonitrile at r.t. Further suitable metal catalysts for said cyclisation reaction include for example Pd(II) catalysts, such as PdCl2(MeCN)2, see Bart C. J. van Esseveldt et al *J. Org. Chem.* 2005, 70, 1791-1795.

Compounds of formula (VII) may be prepared by Sonogashira coupling of a compound of formula (VIII), wherein LG1 is a suitable leaving group such as a halogen atom (e.g. chlorine),

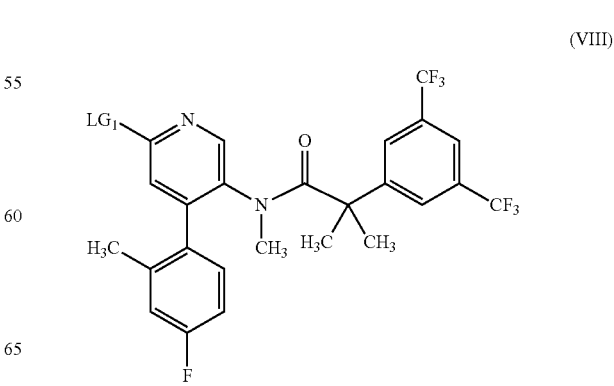

(VIII)

-continued

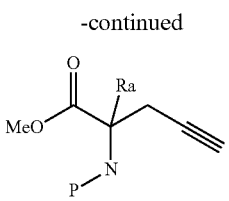

(IX)

with an acetylene amino ester (IX), wherein P is a nitrogen protecting group and Ra is hydrogen or $C_{1-4}$ alkyl, in the presence of CuI. This reaction may be carried out in an inert solvent, in the presence of palladium (0). Examples of suitable palladium catalysts include but are not limited to, tetrakis(triphenylphosphine)palladium (0) and tris(dibenzylideneacetone)dipalladium (0). It is also possible to generate the palladium (0) catalyst in situ using palladium (II) sources. Examples of suitable palladium (II) sources include but are not limited to, palladium (II) acetate, palladium (II) chloride, palladium (II) trifluoroacetate, dichlorobis(triphenyl-phosphine)palladium (II), and bis(diphenylphosphino-ferrocene)palladium (II) dichloride. Suitable solvents for this reaction include but are not limited to triethylamine, diisopropylamine, N,N-dimethylformamide, tetrahydrofuran, dioxane, toluene, benzene, 1,2-dimethoxothane, and 1-methyl-2-pyrrolidinone. Bases and phosphines may be included as additives in the reaction if desired. Examples of suitable bases include trialkylamines such for example triethylamine, diisopropylamine and mixtures thereof. Examples of suitable phosphine additives include but are not limited to triphenylphosphine, tributylphosphine and ethylenebis(diphenylphosphine).

Compounds of formula (VI), wherein LG is a mesilate group, may be obtained in accordance with the following scheme:

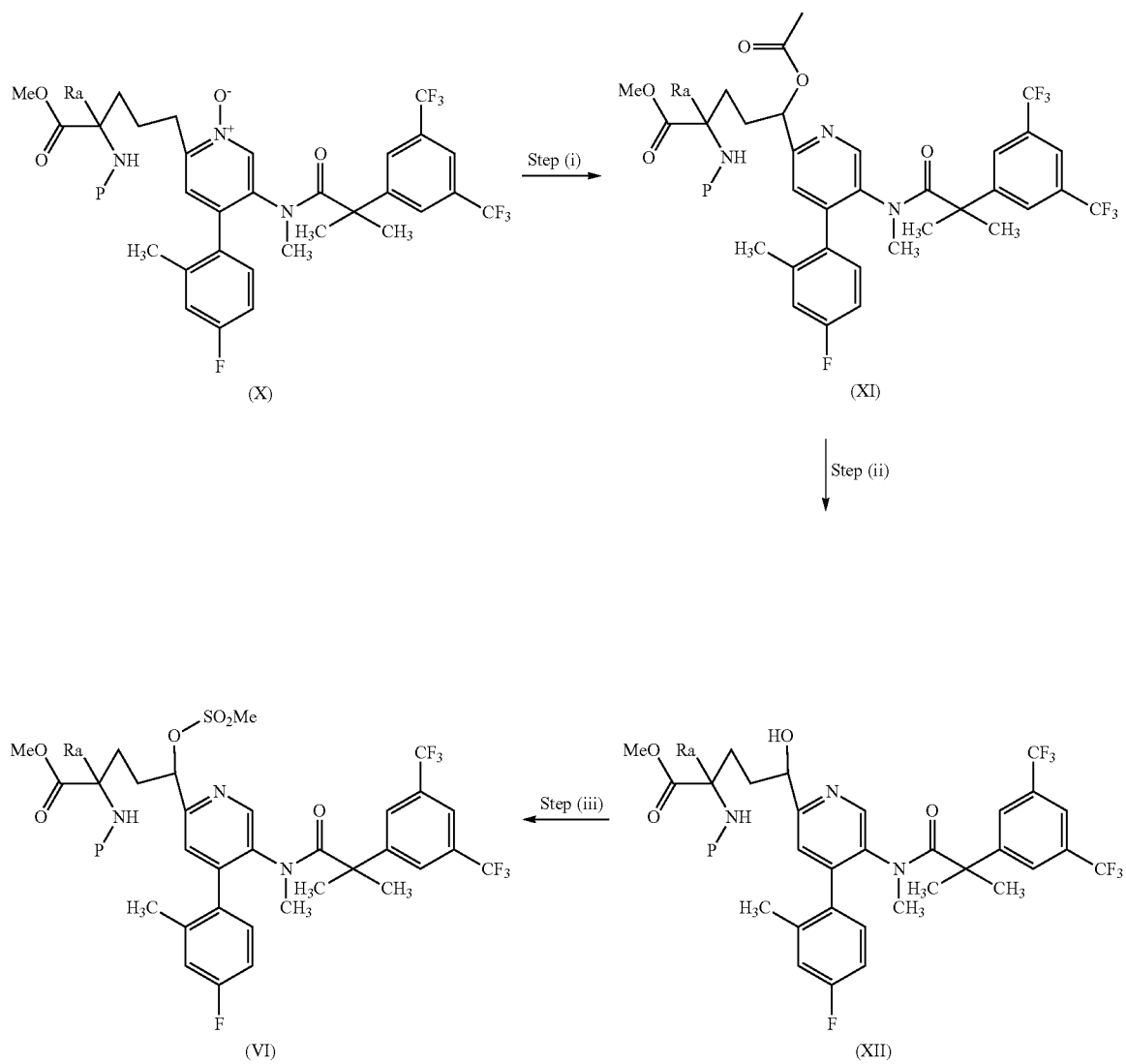

Step (i) typically comprises reacting a N-oxide of formula (X), wherein Ra is hydrogen or C 1-4 alkyl and P is a nitrogen group, with acetic anhydride at 100° C. see V. Boekelheide *Journal of American Chemical Society* 1954, vol 76 pages 1286-1291.

Step (ii) typically comprises base catalysed hydrolysis of a compound of formula (XI) with $Na_2CO_3$ in the presence of a suitable solvent such as an alcohol i.e. methanol.

Step (iii) typically comprises reacting a compound of formula (XII) with methanesulfonyl chloride in the presence of a suitable solvent such as dichloromethane and a suitable base such as triethylamine.

Compounds of formula (X) may be prepared in accordance with the following scheme:

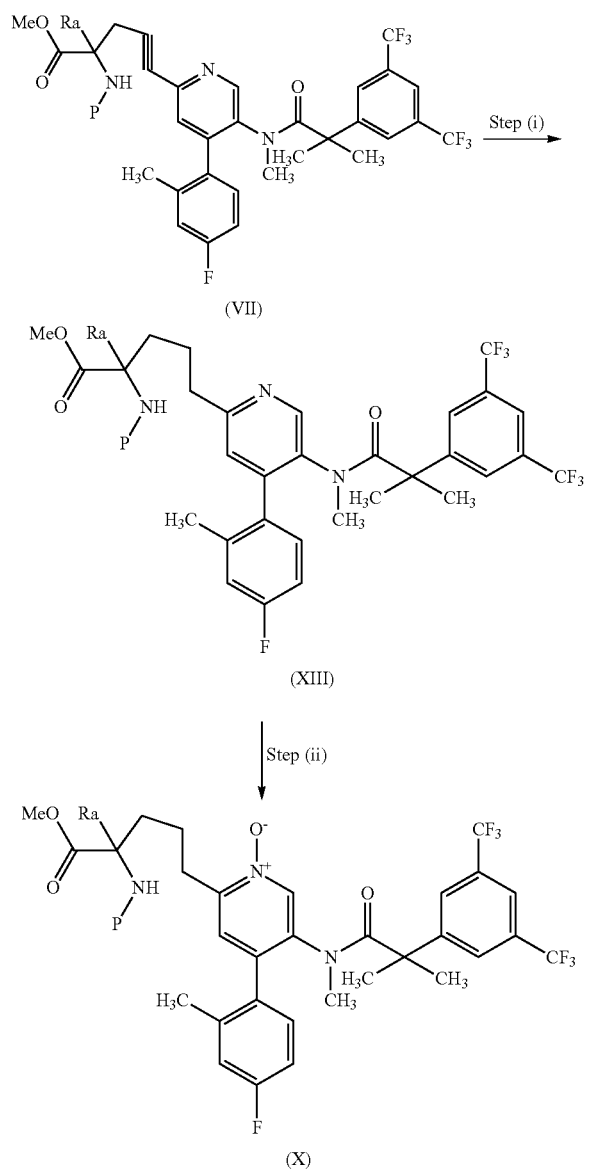

Step (i) typically comprises reduction of a acetylene amino ester (VII), wherein Ra is hydrogen or $C_{1-4}$ alkyl and P is a nitrogen group, using conventional reduction techniques suitable for such compounds. Suitable reduction conditions will be apparent to those skilled in the art of organic synthesis and may include, for example, palladium on carbon under a hydrogen atmosphere.

Step (ii) typically comprises oxidation of (XIII) employing a suitable oxidising agent such as 3-chloroperoxybenzoic acid (m-CPBA), in a suitable solvent such as dichloromethane, at a suitable temperature, such as room temperature.

Compounds of formula (IX) may be prepared by the corresponding propargyl glycine derivate (XIV), wherein Ra is hydrogen or $C_{1-4}$ alkyl, using the conventional technique known to the skilled person for obtaining ester from acid and for protecting nitrogen group, see Floris P. J. T. Rutjes, *Advanced Synthesis & Catalysis,* 346(7), 823-834; 2004.

Compounds of formula (III) may be prepared by reaction of a compound of formula (V), wherein Ra is $C_{1-4}$ alkyl with ammonia in a suitable solvent such as methanol at suitable temperature such as 20-70° C.

Where it is desired to isolate the compound of formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compounds of formula (I) using conventional methods.

When a specific enantiomer or diasteroisomer of the compound of formula (I) is required, this may be obtained, for example, from the appropriate optically active starting material (XIV), i.e. a L-propargyl glycine derivative (XIVa) and a D-propargyl glycine derivate (XIVb), wherein Ra is hydrogen or is $C_{1-4}$ alkyl, using any of the general processes described herein.

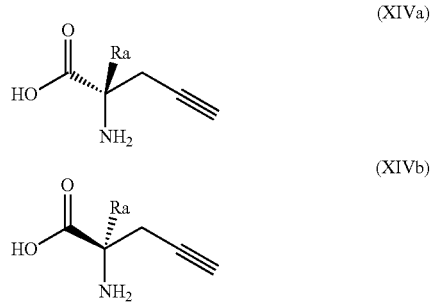

Thus, for example diastereoisomers (Ia) and (Ib) may be obtained starting from (XIVa), wherein Ra is $C_{1-4}$ alkyl, and diastereoisomers (Ic) and (Id) may be obtained starting from (XIVb), wherein Ra is $C_{1-4}$ alkyl, using the general processes described herein followed by separation of the mixture of diastereoisomers at a convenient point of the process. Alternatively diastereoisomers (Ia) (Ib) (Ic) and (Id) may be obtained, for example, starting from (XIVa) or (XIVb), wherein Ra is hydrogen, using the general processes described herein followed by separation of the mixture of diastereoisomers at a convenient point of the process.

Thus, diastereoisomers of formula (II) namely (IIa) and (IIb) may be obtained from intermediate (Va), wherein R is $C_{1-4}$ alkyl, in accordance with the following scheme,

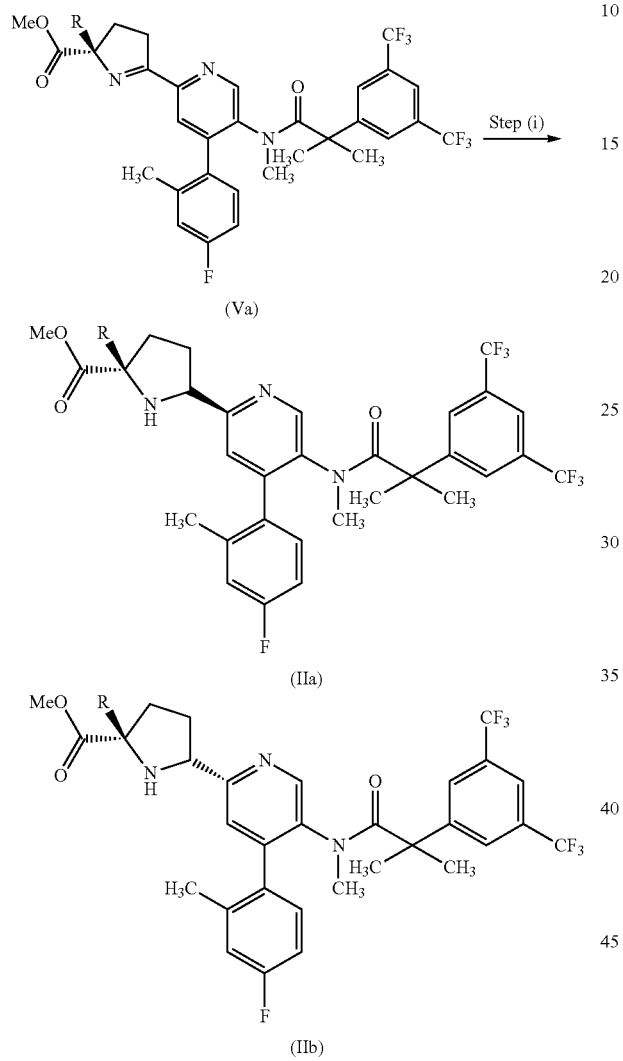

and diastereoisomers (IIc) and (IId) may be obtained from intermediate (Vb), wherein R is $C_{1-4}$ alkyl, in accordance with the following scheme.

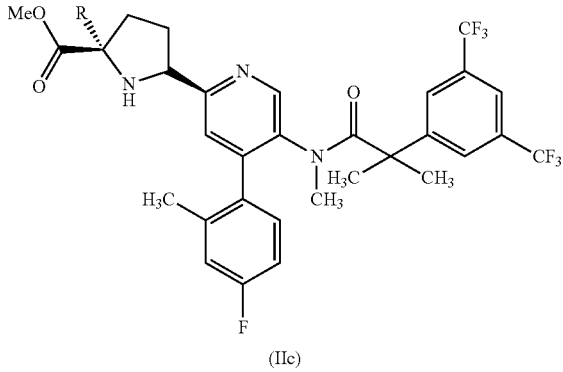

Steps (i) and (ii) comprise the reduction to obtain a mixture of two diastereoisomers (IIa) and (IIb), and a mixture of two diastereoisomers (IIc) and (IId) respectively, using the same procedure described herein for preparing compounds (II) from compounds (V), followed by separation of said mixture of diastereoisomers into the single diastereoisomer by conventional means such as chromatography or crystallisation.

In a further embodiment of the invention diastereoisomers (IIa) and (IIb) may be obtained from intermediate (Via), wherein R is $C_{1-4}$ alkyl, in accordance with the following scheme,

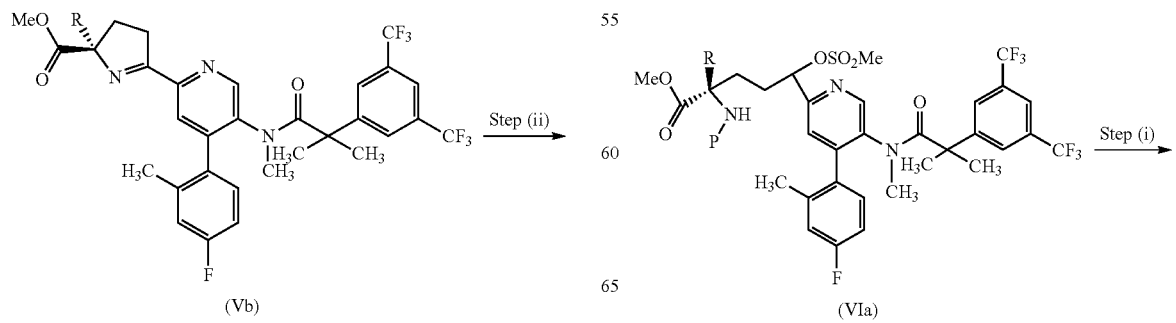

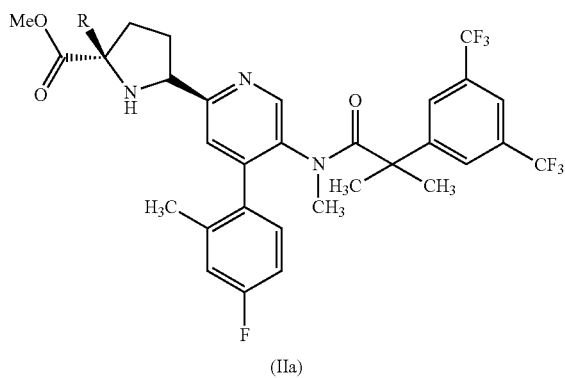

(IIa)

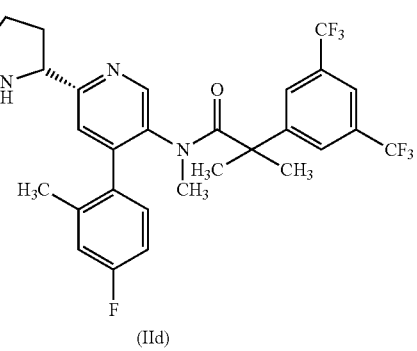

(IId)

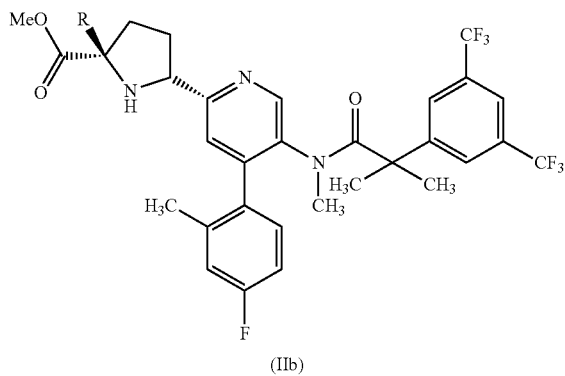

(IIb)

Steps (i) and (ii) comprise the cyclisation to obtain a mixture of two diastereoisomers (IIa) and (IIb) and a mixture of the two diastereoisomers (IIc) and (IId), using the same procedure described herein for preparing compounds (II) from compounds (VI), followed by separation of said mixture of diastereoisomers by conventional means such as chromatography or crystallisation.

Steps (i) and (i) also comprise the removal of the protecting group P.

In a further embodiment of the invention diastereoisomers (IId) and (IIb) may be obtained from intermediate (IVa) in accordance with the following scheme.

and diastereoisomers (IIc) and (IId) may be obtained from intermediate (VIb), wherein R is $C_{1-4}$ alkyl, in accordance with the following scheme.

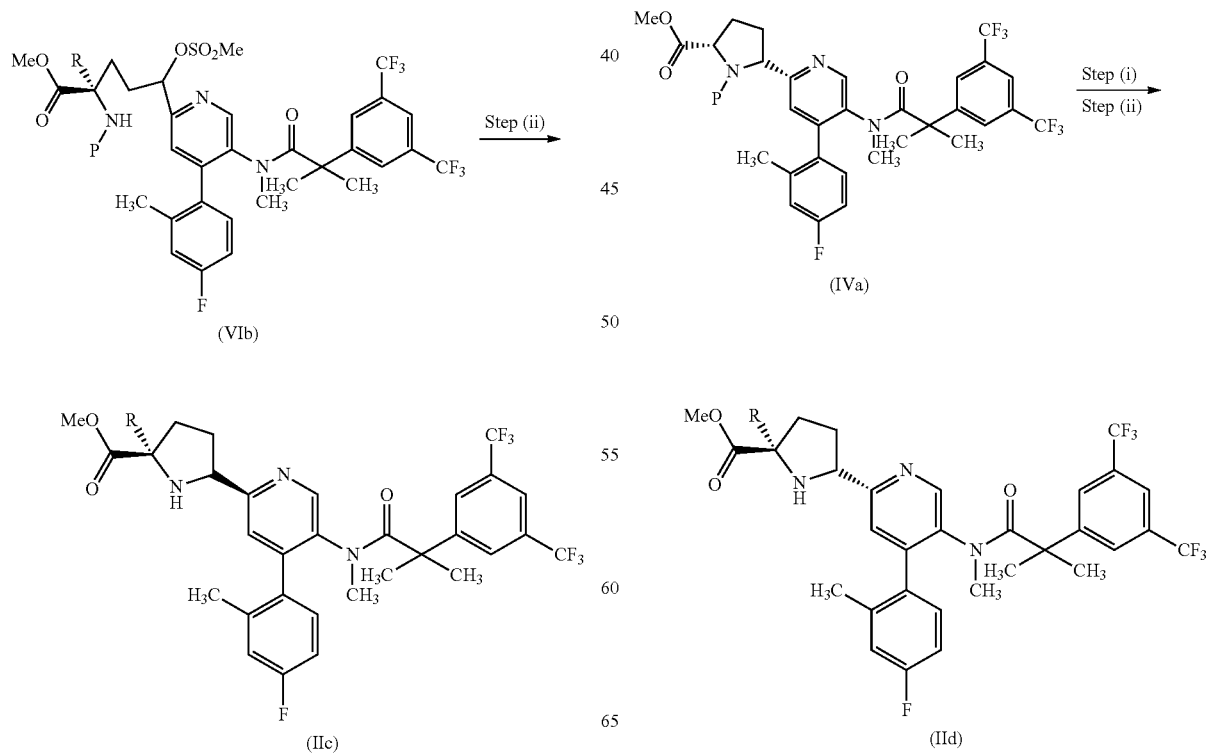

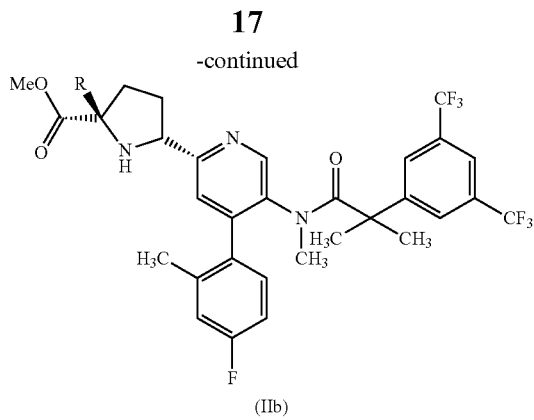

(IIb)

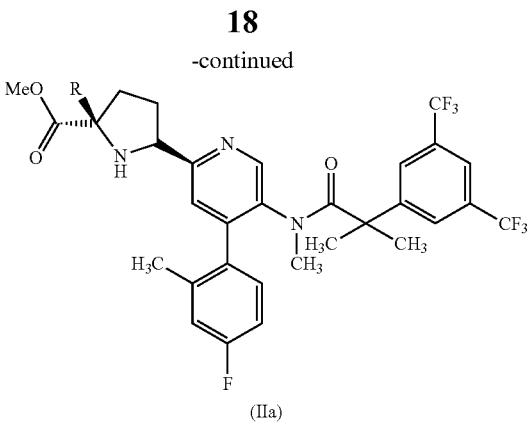

(IIa)

Step (i) comprises the alkylation reaction with a suitable electrophile R—X, wherein R is $C_{1-4}$ alkyl and X is a suitable leaving group, to obtain a mixture of two N-protected diastereoisomers (IId) and (IIb), using the same procedure described herein for preparing compounds (II) from compounds (IV), followed by separation of said mixture of diastereoisomers by conventional means such as chromatography or crystallisation.

Step (ii) comprises the removal of the protecting group P.

In a further embodiment of the invention diastereoisomers (IIa) and (IIc) may be obtained from intermediate (IVb) in accordance with the following scheme.

Step (i) comprises the alkylation reaction with a suitable electrophile R—X, wherein R is $C_{1-4}$ alkyl and X is a suitable leaving group, to obtain a mixture of two n-protected diastereoisomers (IIc) and (IIa), using the same procedure described herein for preparing compound (II) from compound (IV), followed by separation of said mixture of diastereoisomers by conventional means such as chromatography or crystallisation. Step (ii) comprises the removal of the protecting group P.

Compounds (IIa), (IIb), (IIc) and (IId) may be converted to (Ia), (Ib), (Ic) and (Id) using the same procedure described herein to obtain a compound of formula (I) from (II).

In a further embodiment the diastereoisomers of formula (I) namely (Ia) and (Ib) may be obtained from diastereoisomer (IIIa), wherein R is $C_{1-4}$ alkyl, in accordance with the following scheme by reduction to obtain a mixture of two diastereoisomers (Ia) and (Ib), using the same procedure described herein for preparing compound (I) from compound (III), followed by separation of said mixture of diastereoisomers by conventional means such as chromatography or crystallisation.

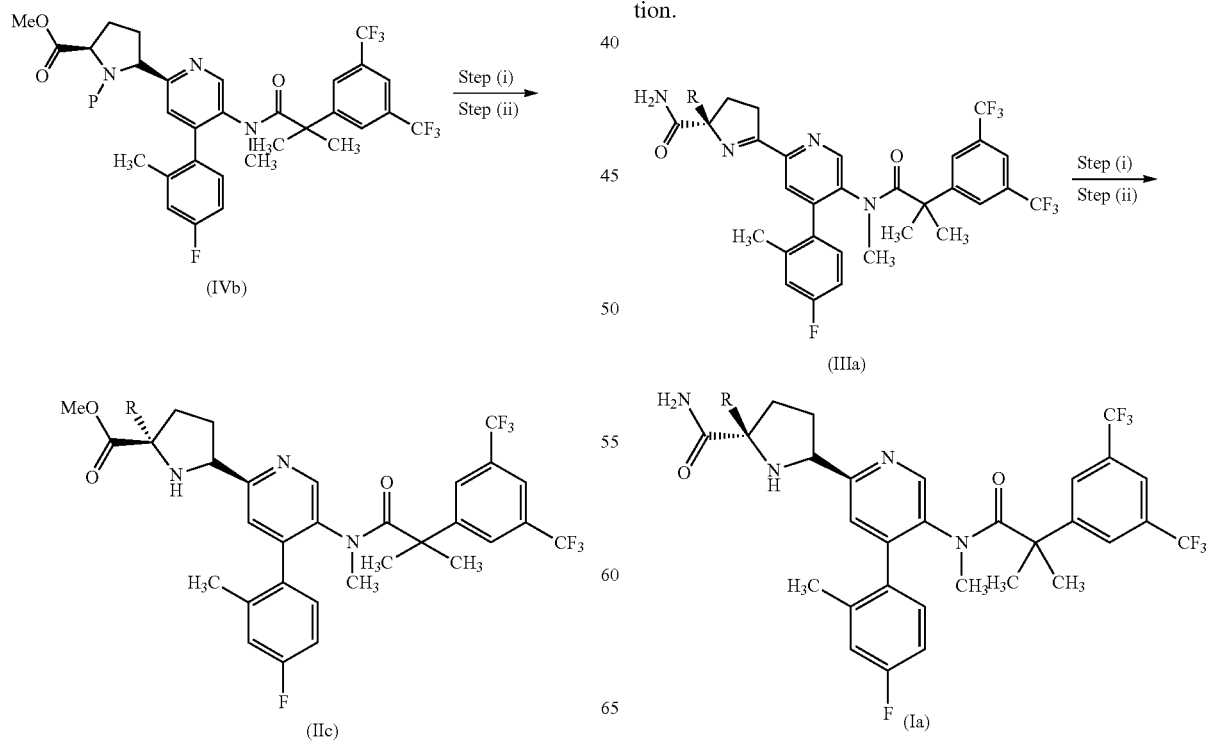

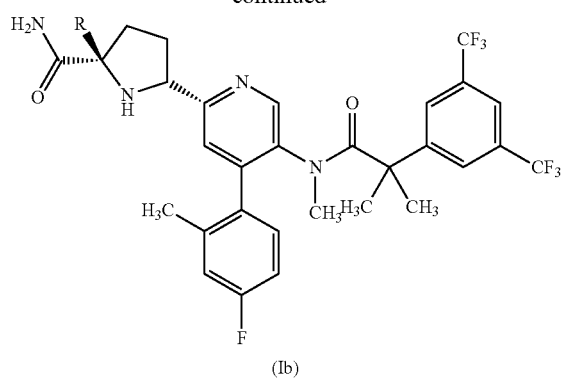

(Ib)

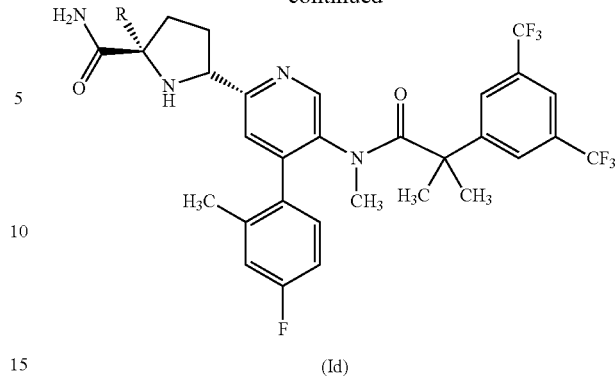

(Id)

Thus diasteroisomers of formula (I) namely (Ic) and (Id) may be obtained from diasteroisomer (IIIb), wherein R is $C_{1-4}$ alkyl, in accordance with the following scheme by reduction to obtain a mixture of two diastereoisomers (Ic) and (Id), using the same procedure described herein for preparing compound (I) from compound (III), followed by separation of said mixture of diastereoisomers by conventional means such as chromatography or crystallisation.

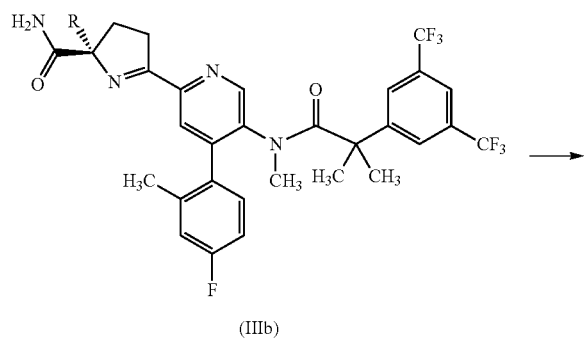

(IIIb)

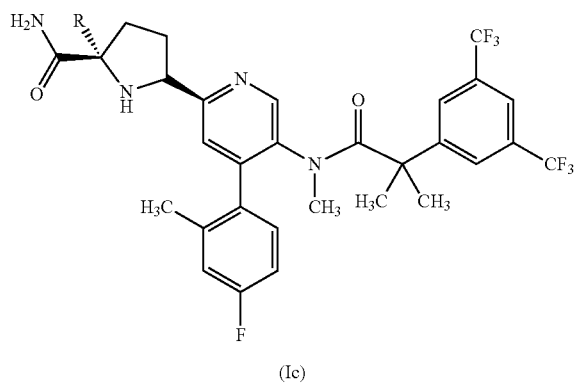

(Ic)

Compounds of formula (VIII) may be prepared in accordance with the methodology provided in WO 2005/002577.

Compound (XIV) is known compound (Martin, et al. Angewandte Chemie, International Edition (2006), 45(9), 1439-1442.).

Compounds of formula (XIVa) or (XIVb) may be obtained from the racemate compound (XIV) using conventional method known to separate enantiomers from a racemic mixture. Alternatively, compounds of formula (XIVa) or (XIVb), wherein Ra is hydrogen are commercially available for example from Bachem AG, CSPS Pharmaceuticals, Inc and Nagase & Co., Ltd. Compounds of formula (XIVb) wherein Ra is methyl is commercially available from Nagase & Co., Ltd.

Compounds of formula (I) and its pharmaceutically acceptable salts have affinity for and are specific antagonists of tachykinins, including substance P and other neurokinins.

Tachykinins are a family of peptides that share a common carboxyl-terminal sequence (Phe-X-Gly-Leu-Met-NH2). They are actively involved in the physiology of both lower and advanced life forms. In mammalian life forms, the main tachykinins are substance P(SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1(SP-preferring), NK2 (NKA-preferring) and NK3 (NKB-preferring) which are widely distributed throughout the central nervous (CNS) and peripheral nervous system.

Particularly, compounds of the invention are selective antagonists of the NK1 receptor.

The selectivity of compounds of the invention on the NK1 receptor is more than 100 fold with respect to NK2 and NK3 receptors.

Compounds of the invention are useful in the treatment of conditions for which antagonism of NK1 receptor is beneficial Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Compounds of formula (I) or pharmaceutically acceptable salts thereof may be of use in the treatment of the following disorders:

Depression and mood disorders including Major Depressive Episode, Manic Episode, Mixed Episode and Hypo manic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypo manic Episodes) (296.89), Cyclothymiacs Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (30460), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Sleep disorders including primary sleep disorders such as Dyssomnias such as Primary Insomnia (307.42), Primary Hypersomnia (307.44), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9):

Compounds of the invention may be useful for Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

Compounds of the invention may be also useful as anti-inflammatory agents. In particular, they may be useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis, overactive bladder and urge incontinence; and eye and dental inflammation.

Compounds of the invention may be also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. Compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral, e.g. myocardial infarction or peritonitis; migraine; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia.

Compounds of the invention may be also useful in the treatment of gastrointestinal disorders such as irritable bowel syndrome, gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia (such as ulcer-like dyspepsia, dysmotility-like dyspepsia and unspecified dyspepsia) chronic constipation; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Within the context of the present invention, the term "pain" includes: chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with cluster and chronic daily headache; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; dysmenorrhea; neuralgia; fibromyalgia syndrome; complex regional pain syndrome (CRPS types I and II); neuropathic pain syndromes (including diabetic neuropathy; chemoterapeutically induced neuropathic pain; sciatica; non-specific lower back pain; multiple sclerosis pain; HIV-related neuropathy; post-herpetic neuralgia; trigeminal neuralgia); and pain resulting from physical trauma, amputation, cancer, toxins or chronic inflammatory conditions.

Compounds of the invention may be useful in cachexia including systemic cachexia, cachexia secondary to infection or malignancy and cachexia secondary to AIDS, renal insufficiency, cardiac insufficiency and pulmonary insufficiency.

Compounds of the invention may be also useful for treatment of patients suffering from anorexia-cachexia syndrome which is a debilitating condition characterizing the clinical journey of patients suffering from chronic diseases including cancer, chronic obstructive pulmonary disease, tuberculosis, chronic heart failure, and end-stage renal insufficiency.

All of the various forms and sub-forms of the disorders mentioned herein are contemplated as part of the present invention.

Compounds of the invention are particularly useful in the treatment or prevention of depression, anxiety, sleep disorders or emesis.

The invention therefore provides a compound of formula (I) or a pharmaceutically acceptable salt thereof for use in therapy.

Thus, the invention also provides a compound of formula (I) or a pharmaceutically acceptable salt thereof, for use as a therapeutic substance in the treatment or prophylaxis of the above disorders.

The invention further provides a compound of formula (I) or a pharmaceutically acceptable salt thereof, for use in the treatment of depression, anxiety, sleep disorders or emesis.

The invention further provides a method of treatment or prophylaxis of conditions mediated by tachykinins, in mammals including humans, which comprises administering to the sufferer a therapeutically effective amount of a compound of formula (I) or a pharmaceutically acceptable salt thereof.

The invention further provides a method of treatment or prophylaxis of conditions for which antagonism of NK1 receptor is beneficial, in mammals including humans, which comprises administering to the sufferer a therapeutically effective amount of a compound of formula (I) or a pharmaceutically acceptable salt thereof.

The invention further provides a method of treatment or prophylaxis of the above disorders, in mammals including humans, which comprises administering to the sufferer a therapeutically effective amount of a compound of formula (I) or a pharmaceutically acceptable salt thereof.

The invention further provides a method of treatment or prophylaxis of depression, anxiety, sleep disorders or emesis in mammals including humans, which comprises administering to the suffer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of conditions mediated by tachykinins.

In another aspect, the invention provides the use of a compound of formula (I) or a pharmaceutically acceptable salt thereof in the manufacture of a medicament for use in the treatment of conditions for which antagonism of NK1 receptor is beneficial.

In another aspect, the invention provides the use of a compound of formula (I) or a pharmaceutically acceptable salt thereof in the manufacture of a medicament for use in the treatment of the above disorders.

In another aspect, the invention provides the use of a compound of formula (I) or a pharmaceutically acceptable salt thereof in the manufacture of a medicament for use in the treatment of depression, anxiety, sleep disorders or emesis.

When used in therapy, the compounds of formula (I) are usually formulated in a standard pharmaceutical composition. Such compositions can be prepared using standard procedures.

The present invention further provides a pharmaceutical composition which comprises a compound of formula (I) or a pharmaceutically acceptable salt thereof and a pharmaceutically acceptable carrier.

The present invention further provides a pharmaceutical composition for use in the treatment of the above disorders which comprises a compound of formula (I) or a pharmaceutically acceptable salt thereof and a pharmaceutically acceptable carrier.

Compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

Compounds of the invention may be used in combination with antidepressants to treat or prevent depression and mood disorders.

Compounds of the invention may be used in combination with an opioid analgesic to treat and prevent pain.

Compounds of the invention may be used in combination with the following agents to treat or prevent bipolar disease: i) mood stabilisers; ii) antipsychotics; and iii) antidepressants.

Compounds of the invention may be used in combination with the following agents to treat or prevent anxiety disorders: i) anxiolytics; and ii) antidepressants.

Compounds of the invention may be used in combination with the following agents to improve nicotine withdrawal and reduce opiate craving: i) nicotine replacement therapy for example a sublingual formulation of nicotine beta-cyclodextrin and nicotine patches; and ii) bupropion.

Compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

Compounds of the invention may be used in combination with the following agents to improve opiate withdrawal and reduce opiate craving: i) oploid mu receptor agonist/opioid kappa receptor antagonist for example buprenorphine; ii) opioid receptor antagonists for example naltrexone; and iii) vasodilatory antihypertensives for example lofexidine.

Compounds of the invention may be used in combination with the following agents to treat or prevent sleep disorders: i) benzodiazepines for example temazepam, lormetazepam, estazolam and triazolam; ii) non-benzodiazepine hypnotics for example zolpidem, zopiclone, zaleplon and indiplon; iii)

barbiturates for example aprobarbital, butabarbital, pentobarbital, secobarbita and phenobarbital; iv) antidepressants; v) other sedative-hypnotics for example chloral hydrate and chlormethiazole.

Compounds of the invention may be used in combination with the following agents to treat anorexia: i) appetite stimulants for example cyroheptidine; ii) antidepressants; iii) antipsychotics; iv) zinc; and v) premenstrual agents for example pyridoxine and progesterones.

Compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstrual agents.

Compounds of the invention may be used in combination with the following agents to treat or prevent autism: i) antipsychotics; ii) antidepressants; iii) anxiolytics; and iv) stimulants for example methylphenidate, amphetamine formulations and pemoline.

Compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

Compounds of the invention may be used in combination with the following agents to treat personality disorders: i) antipsychotics; ii) antidepressants; iii) mood stabilisers; and iv) anxiolytics.

Compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

Compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and bxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and brazepam.

Opioid analgesics include alfentanil, buprenorphine, butorphanol, carfentanil, codeine, diacetylmorphine, dihydrocodeine, fentanyl, hydrocodone, hydromorphone, levorphanol, lofentanil, meperidine, methadone, morphine, nalbuphine, oxycodone, oxymorphone, pentazocine, propoxyphenem, remifentanil and sufentanil.

Compounds of the invention may be used in combination with Na channel blockers to treat epilepsy, depression and mood disorders, psychotic disorders or pain.

Within the context of the combination with Na channel blockers, the term "epilepsy" is intended to include Seizure disorders and epilepsy syndromes. The various types of the Epilepsy and seizures mentioned herein below are contemplated as part of the present invention: partial onset seizures (replacing temporal lobe epilepsy, neocortical epilepsy and Rasumssen's), generalized onset seizures, the seizures of the Lennox Gastaut syndrome (tonic, atonic, myoclonic, atypical absence and generalized tonio-clonic), absence seizure syndromes and juvenile myoclonic epilepsy.

Combination of compounds of the invention with a Na channel blocker may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Within the context of the combination with Na channel blockers the term "psychotic disorder" includes:
i) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the combination with Na channel blockers, the term "pain" includes: chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with cluster and chronic daily headache; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; dysmenorrhea; neuralgia; fibromyalgia syndrome; complex regional pain syndrome (CRPS types I and II); neuropathic pain syndromes (including diabetic neuropathy; chemoterapeutically induced neuropathic pain; sciatica; non-specific lower back pain; multiple sclerosis pain; HIV-related neuropathy; post-herpetic neuralgia; trigeminal neuralgia); and pain resulting from physical trauma, amputation, cancer, toxins or chronic inflammatory conditions.

Within the context of the combination with Na channel blockers the term "depression and mood disorder" includes Depression and mood disorders including Major Depressive Episode, Manic Episode, Mixed Episode and Hypo manic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypo manic Episodes) (296.89), Cyclothymiacs Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

In one embodiment, the "depression and mood disorder" which may be treated by administration of a combination of compounds of the invention with Na channel blockers is a bipolar disorder.

In one embodiment, the combination as herein above defined comprises a Na channel blocker selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof.

In a further embodiment, the combination as herein above defined comprises a Na channel blocker selected from the group consisting of fosphenyloin (Cerebyx™, Prodilantin™, Pro-Epanutin™ or Cereneu™), oxcarbazepine (Trileptal™, Oxrate™ or Wockhardt™) phenyloin, carbamazepine (Carbatrol, Equetro™), lidocaine (ALGRX-3268), Safinamide (NW-1015), Ralfinamide (NW-1029), Lacosamide ((2R)-2-(acetylamino)-3-methoxy-N-(phenylmethyl)propanamide), and rufinamide (RUF-331).

In a further embodiment, the combination as herein above defined comprises a Na channel blocker selected from the group consisting of:
3,5-diamino-6-(2,3-dichlorophenyl)-1,2,4-triazine;
R(−)-2,4-diamino-5-(2,3-dichlorophenyl)-6-fluoromethylpyrimidine;
(2R,5R)-2-(4-{[(2-fluorophenyl)methyl]oxy}phenyl)-1,7-diazaspiro[4.4]nonan-6-one;
(2R,5R)-2-(4-{[(2-fluorophenyl)methyl]oxy}phenyl)-7-methyl-1,7-diazaspiro[4.4]nonan-6-one;
(5R)-5-(4-{[(2-fluorophenyl)methyl]oxy}phenyl)-L-prolinamide
or pharmaceutically acceptable salts or solvates thereof.

In an additional further embodiment, the combination as herein above defined comprises a Na channel blocker which is 3,5-diamino-6-(2,3-dichlorophenyl)-1,2,4-triazine or a pharmaceutically acceptable salt or solvate thereof.

Compound 3,5-diamino-6-(2,3-dichlorophenyl)-1,2,4-triazine and pharmaceutically acceptable salts and solvates thereof are described in EP granted Patent EP0021121B and in U.S. Pat. No. 4,602,017. Compound 3,5-diamino-6-(2,3-dichlorophenyl)-1,2,4-triazine and pharmaceutically acceptable salts and solvates thereof may be prepared by any method described in EP0021121B and U.S. Pat. No. 4,602,017.

In another embodiment, the combination as herein above defined comprises a Na Channel blocker which is R(−)-2,4-diamino-5-(2,3-dichlorophenyl)-6-fluoromethylpyrimidine or a pharmaceutically acceptable salt or solvate thereof.

Compound R(−)-2,4-diamino-5-(2,3-dichlorophenyl)-6-fluoromethylpyrimidine and pharmaceutically acceptable salts and solvates thereof are described in PCT publication No. WO 97/9317, published 13 Mar. 1997. Compound R(−)-2,4-diamino-5-(2,3-dichlorophenyl)-6-fluoromethylpyrimidine and pharmaceutically acceptable salts and solvates thereof may be prepared by any method described in WO 97/9317.

In an additional further embodiment, the combination as herein above defined comprises a Na channel blocker which is (5R)-5-(4-{[(2-fluorophenyl)methyl]oxy}phenyl)-L-prolinamide or a pharmaceutically acceptable salt or solvate thereof.

Compound (5R)-5-(4-{[(2-fluorophenyl)methyl]oxy}phenyl)-L-prolinamide and pharmaceutically acceptable salts and solvates thereof are described in PCT publication No. WO2007/042239. Compound (5R)-5-(4-{[(2-fluorophenyl)methyl]oxy}phenyl)-L-prolinamide or pharmaceutically acceptable salts and solvates thereof may be prepared by any method described in WO2007/042239.

In an additional further embodiment, the combination as herein above defined comprises a Na Channel blocker which is (2R,5R)-2-(4-{[(2-fluorophenyl)methyl]oxy}phenyl)-7-methyl-1,7-diazaspiro[4.4]nonan-6-one or a pharmaceutically acceptable salt or solvate thereof. Compound (2R,5R)-2-(4-{[(2-fluorophenyl)methyl]oxy}phenyl)-7-methyl-1,7-diazaspiro[4.4]nonan-6-one and pharmaceutically acceptable salts and solvates thereof are described in PCT publication No. WO2007/042240. Compound (2R,5R)-2-(4-{[(2-fluorophenyl)methyl]oxy}phenyl)-7-methyl-1,7-diazaspiro[4.4]nonan-6-one and pharmaceutically acceptable salts and solvates thereof may be prepared by any method described in WO2007/042240.

In one embodiment, the combination of a compound of the invention with a Na channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide, or a pharmaceutically acceptable salt or solvate thereof.

The invention thus provides, in a further aspect, a combination comprising a compound of the invention together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of the invention is used in combination with a second therapeutic agent active against the same disease state the dose of each compound may differ from that when the compound is used alone. Appropriate doses will be madly appreciated by those skilled in the art.

Thus, in one embodiment, a combination of a compound of the invention with a Na channel blocker is provided, wherein at least one of them is at sub therapeutic dose.

A subtherapeutic dose is intended to mean a dose of a drug below that required to produce significant clinical benefit for the patient when administered alone.

In one embodiment, the combination of a compound of the invention with a Na Channel blocker, comprises a Na Channel blocker, at subtherapeutic dose, which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and a compound of the invention.

In another embodiment, the combination of a compound of the invention with a Na Channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and a compound of the invention, at sub therapeutic dose.

In a further embodiment, the combination of a compound of the invention with a Na channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and a compound of formula (I) or a pharmaceutically acceptable salt or solvate thereof; such compound of formula (I) and Na Channel blocker compound being both administered at sub therapeutic dose.

In one embodiment, the combination of a compound of the invention with a Na Channel blocker, comprises a Na Channel blocker, at subtherapeutic dose, which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide or a pharmaceutically acceptable salt or solvate thereof.

In another embodiment, the combination of a compound of the invention with a Na Channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW- 1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt or solvate thereof; and ((5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide or a pharmaceutically acceptable salt or solvate thereof, at sub therapeutic dose.

In a further embodiment, the combination of a compound of the invention with a Na Channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); Lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt or solvate thereof; and ((5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide or a pharmaceutically acceptable salt thereof; such compound (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide and a Na Channel blocker compound being both administered at sub therapeutic dose.

Thus, the invention also provides a combination of a compound of the invention with a Na channel blocker compound, for use in therapy.

Thus, the invention also provides a combination of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide or a pharmaceutically acceptable salt thereof with a Na channel blocker compound which is selected from the group consisting of: 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt or solvate thereof; for use as a therapeutic substance in the treatment or prophylaxis of epilepsy, depression and mood disorders, psychotic disorders or pain.

In one embodiment, the invention provides a combination of a compound of the invention with a Na channel blocker compound, for use as a therapeutic substance in the treatment or prophylaxis of epilepsy, depression and mood disorders, psychotic disorders or pain.

In an embodiment, the invention provides a combination of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide or a pharmaceutically acceptable salt thereof with a Na channel blocker compound, which is selected from the group consisting of: 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethyl pyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt thereof; for use as a therapeutic substance in the treatment or prophylaxis of epilepsy, depression and mood disorders, psychotic disorders or pain.

The invention further provides a method of treatment or prophylaxis of epilepsy, depression and mood disorders, psychotic disorders or pain, in mammals including humans, which comprises administering to the sufferer a therapeutically effective amount of a combination of a compound of the invention with a Na channel blocker compound.

The invention further provides a method of treatment or prophylaxis of epilepsy, depression and mood disorders, psychotic disorders or pain, in mammals including humans, which comprises administering to the sufferer a therapeutically effective amount of a combination of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide or a pharmaceutically acceptable salt thereof with a Na channel blocker compound, which is selected from the group consisting of: 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethyl pyramiding, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-polyamide or a pharmaceutically acceptable salt thereof.

In another aspect, the invention provides the use of a combination of a compound of the invention with a Na channel blocker compound in the manufacture of a medicament for use in the treatment of epilepsy, depression and mood disorders, psychotic disorders or pain.

In another aspect, the invention provides the use of a combination of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide or a pharmaceutically acceptable salt thereof with a Na channel blocker compound, which is selected from the group consisting of: 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt thereof, in the manufacture of a medicament for use in the treatment of epilepsy, depression and mood disorders, psychotic disorders or pain.

When used in therapy, combinations of a compound of the invention with a Na channel blocker compound are usually formulated in a standard pharmaceutical composition. Such compositions can be prepared using standard procedures.

The present invention further provides a pharmaceutical composition which comprises a combination of a compound of the invention with a Na channel blocker compound and a pharmaceutically acceptable carrier.

The present invention further provides a pharmaceutical composition for use in the treatment of epilepsy, depression and mood disorders, psychotic disorders or pain which comprises combinations of a compound of the invention with a Na channel blocker compound and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or a pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Compositions suitable for transdermal administration include ointments, gels and patches.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 1.0 to 200 mg, more suitably 5 to 100 mg, and such unit doses may be administered more than once a day, for example two or three a day. Such therapy may extend for a number of weeks or months.

EXPERIMENTAL

The following Intermediates and Examples illustrate the preparation of compounds of the invention.

In the procedures that follow, after each starting material, reference to a description is typically provided. This is provided merely for assistance to the skilled chemist. The starting material may not necessarily have been prepared from the batch referred to.

The relative configuration (absolute on the basis of the fixed configuration of the stereocenter at 5-position as shown below) of the stereocenter at the 2-position has been assigned on the basis of 2D $^1$H,$^1$H-ROESY NMR, 2D $^1$H,$^1$H-NOESY NMR or 1D $^1$H,$^1$H-NOE difference NMR spectroscopy experiments.

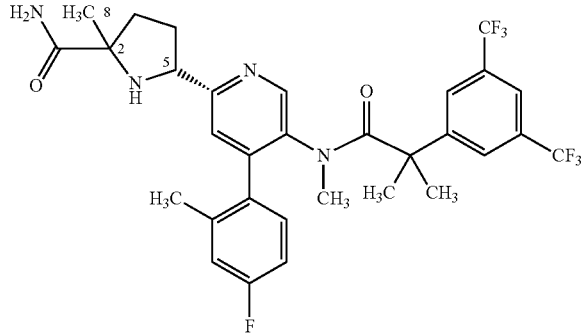

Compounds are named using ACD/Name PRO 6.02 chemical naming software (Advanced Chemistry Development Inc., Toronto, Ontario, M5H2L3, Canada).

The yields were calculated assuming that products were 100% pure ř not stated otherwise.

Proton Magnetic Resonance (NMR) spectra were recorded either on Varian instruments at 300, 400, 500 or 600 MHz, or on a Bruker instrument at 300 MHz and 400 MHz. Chemical shifts are reported in ppm (δ) using the residual solvent line as internal standard. Splitting patterns are designed as s, singlet; d, doublet; t, triplet; q, quartet m, multiplet; b, broad. The NMR spectra were recorded at a temperature ranging from 25 to 90° C. When more than one conformer was detected the chemical shifts for the most abundant one are reported.

HPLC analyses indicated by HPLC (walk-up): rt=x min, were performed on an Agilent 1100 series instrument using a Luna 3u C18(2) 100A column (50×2.0 mm, 3 μm particle size) [Mobile phase and Gradient: 100% (water+0.05% TFA) to 95% (acetonitrile+0.05% TFA) in 8 min. Column T=40° C. Flow rate=1 mL/min. UV detection wavelength=220 nm].

The usage of this methodology is indicated by "HPLC" in the analytic characterization of the described compounds.

Total ion current (TIC) and DAD UV chromatographic traces together with MS and UV spectra associated with the peaks were acquired on a UPLC/MS Acquity™ system equipped with 2996 PDA detector and coupled ID a Waters Micromass ZQ™ mass spectrometer operating in positive or negative electrospray ionisation mode [LC/MS-ES (+ or −): analyses performed using an Acquity™ UPLC BEH C18 column (50×2.1 mm, 1.7 μm particle size). Mobile phase: A—water+0.1% HCO$_2$H/B—CH3CN+0.06% HCO$_2$H. Gradient: t=0 min 3% B, t=0.05 min 6% B, t=0.57 min 70% B, t=1.06 min 99% B lasting for 0.389 min, t=1.45 min 3% B, stop time 1.5 min. Column T=40° C. Flow rate=1.0 mL/min. Mass range: ES (+): 100-1000 amu. ES (−): 100-800 amu. UV detection range: 210-350 nm. The usage of this methodology is indicated by "UPLC" in the analytic characterization of the described compounds.

Direct infusion Mass spectra (MS) were acquired on a Agilent MSD 1100 Mass Spectrometer, operating in ES (+) and ES (−) ionization mode [ES (+): Mass range: 100-1000 amu. Infusion solvent: water+0.1% HCO2H/CH3CN 50/50. ES (−): Mass range: 100-1000 amu. Infusion solvent: water+0.05% NH4OH/CH3CN 50/50] (the usage of this methodology is indicated by "MS" in the analytic characterization of the described compounds).

Unless otherwise stated, the differential scanning calorimetry (DSC) was carried out on a TA Q1000 system at a scan rate of 10° C. per minute, using a sample size of between 1 and 2 mg.

For reactions involving microwave irradiation, a Personal Chemistry Emrys™ Optimizer was used.

Flash silica gel chromatography was carried out on silica gel 230-400 mesh (supplied by Merck AG Darmstadt, Germany) or over Varian Mega Be—Si pre-packed cartridges or over pre-packed Biotage silica cartridges or over pre-packed RediSep silica cartridges.

SPE-SCX cartridges are ion exchange solid phase extraction columns supplied by Varian. The eluent used with SPE-SCX cartridges is methanol followed by 2N ammonia solution in methanol.

In a number of preparations purification was performed using either Biotage manual flash chromatography (Flash+) or automatic flash chromatography on SPX (Biotage) system using Biotage Silica cartridges, or automatic flash chromatography on Companion CombiFlash (ISCO) using RediSep Silica cartridges.

SPE-Si cartridges are silica solid phase extraction columns supplied by Varian.

The X-ray powder diffraction (XRPD) analysis and was performed on a PANalytical X'Pert Pro powder diffractometer, model PW3040/60, serial number DY1379 using an X'Celerabr detector. The acquisition conditions were: radiation: Cu Kα, generator tension: 40 kV, generator current: 45 mA, start angle: 2.0 °2Theta, end angle: 40.0 °2Theta, step size: 0.0167 °2Theta per step, time: 31.75 seconds. Sample Rotation: 1 s revolution time, incident beam optics: nickel filter, 0.02 radian soller slits, 10 mm beam mask, automatic divergence slits (set to irradiated length of 10 mm), beam knife diffracted beam optics: automatic anti scatter slits (set to irradiated length of 10 mm), 0.02 radian seller slits. The sample was presented using a zero background plate.

The following table lists the abbreviations used:

| | |
|---|---|
| AgOTf | Silver (I) trifluoromethanesulfonate |
| BH3•THF | Borane Tetrahydrofuran complex |
| Boc-Anhydride | Di-tert-butyl dicarbonate |
| CDCl3 | Chloroform-d |
| DCM | Dichloromethane |
| DiPA | Diisopropylamine |
| DIPEA | Diisopropylethylamine |
| DMF | Dimethylformamide |
| DMSO | Dimethyl sulfoxide |
| EtOAc | Ethyl acetate |
| HCl | Hydrochloric acid |
| MeOH | Methanol |
| Na$_2$SO$_4$ | Sodium sulfate |
| NaHCO$_3$ | Sodium bicarbonate |
| THF | Tetrahydrofuran |
| TFA | Trifluoroacetic acid |
| TEA | Triethylamine |
| CD | Circular dicroism |
| HPLC | High Performance Liquid Chromatography |
| UPLC | Ultra Performance Liquid Chromatography |
| DAD | Diode Array Detector |
| TBME | Tertbutylmethylether |
| h | hour |
| min | minute |
| r.t. | room temperature |

Intermediate 1 methyl (2S)-2-({[(1,1-dimethylethyl)oxy]carbonyl}amino)-4-pentynoate

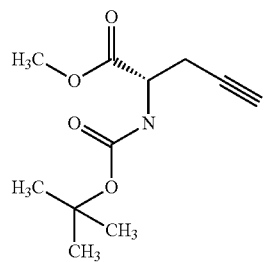 [SMILES: C#CC[C@H](NC(=O)OC(C)(C)C)C(=O)OC]

To a solution of (2S)-2-amino-4-pentynoic acid (Bachem AG, 10 g, 88 mmol) in methanol (200 ml) thionyl chloride (30 ml, 411 mmol) was added dropwise, at 0° C. and the reaction mixture was stirred overnight at r.t. The solvent and the excess of thionyl chloride were evaporated and the residue was dissolved in 1,4-dioxane (150 ml)/NaHCO$_3$ sat. sol. (100 ml); a solution of boc-anhydride (22.17 ml, 95 mmol) in dioxane (20 ml) was added dropwise and there action mixture was stirred for 3 hours at r.t. The mixture was extracted with ethyl acetate (3×200 ml), the combined organic layers were dried (Na$_2$SO$_4$), filtered and evaporated to afford the title compound (20 g, 88 mmol, 100% yield) as a colourless oil. $^1$H NMR (400 MHz, CDCl$_3$) δ(ppm): 5.35 (m, 1H), 4.52 (m, 1H), 3.79 (s, 3H), 2.75 (m, 2H), 2.05 (s, 1H), 1.47 (s, 9H). UPLC: Rt 0.65 min, m/z 228 [M+H$^+$]. and 128 [M-BOC+H$^+$].

Chiral analysis, chromatographic conditions: [Column Chiralcel OJ-H (25×0.46 cm), 5μ; mobile phase: n-hexane/2- propanol 85/15% v/v; Flow rate 1.0 ml/min; DAD 215 nm, CD 225 nm] Rt 5.5 min, 100% e.e.

Intermediate 2 methyl (2S)-5-[5-[{2-[3,5-bis(trifluoromethyl)phenyl]-2-methylpropanoyl}(methyl)amino]-4-(4-fluoro-2-methylphenyl)-2-pyridinyl]-2-({[(1,1-dimethylethyl)oxy]carbonyl}amino)-4-pentynoate

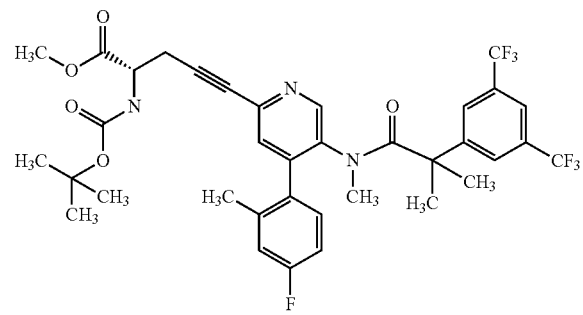 [SMILES: COC(=O)[C@H](CC#Cc1cc(-c2ccc(F)cc2C)c(N(C)C(=O)C(C)(C)c2cc(C(F)(F)F)cc(C(F)(F)F)c2)cn1)NC(=O)OC(C)(C)C]

A solution of 2-[3,5-bis(trifluoromethyl)phenyl]-N-[6-chloro-4-(4-fluoro-2-methylphenyl)-3-pyridinyl]-N,2-dimethylpropanamide (WO2005/002577 intermediate 4D, 1 g, 1.877 mmol), methyl (2S)-2-({[(1,1-dimethylethyl)oxy]carbonyl}amino)-4-pentynoate (Intermediate 1, 1.279 g, 5.63 mmol), Pd(PPh$_3$)$_2$Cl$_2$ (0.066 g, 0.094 mmol), copper(I) iodide (0.018 g, 0.094 mmol), triphenylphosphine (0.049 g, 0.188 mmol) in triethylamine (2 ml)/diisopropylamine (8 ml) was heated at 100° C. under microwave irradiation for 30 mins. The solvents were evaporated and the residue was purified by flash chromatography (Biotage system) on silica gel using a column 40+M and cyclohexane to cyclohexane/ethyl acetate 7:3 as eluent to afford the title compound (750 mg, 1.036 mmol, 55.2% yield) as a white solid. UPLC: Rt 1.02 min, m/z 724 [M+H]$^+$.

Intermediate 3 methyl (2S)-5-[5-[{2-[3,5-bis(trifluoromethyl)phenyl]-2-methylpropanoyl}(methyl)amino]-4-(4-fluoro-2-methylphenyl)-2-pyridinyl]-3,4-dihydro-2H-pyrrole-2-carboxylate

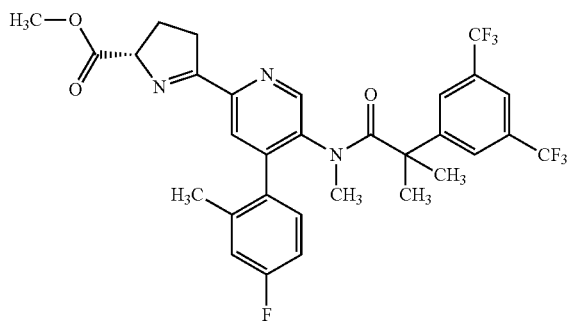 [SMILES: COC(=O)[C@@H]1CCC(c2cc(-c3ccc(F)cc3C)c(N(C)C(=O)C(C)(C)c3cc(C(F)(F)F)cc(C(F)(F)F)c3)cn2)=N1]

To a solution of methyl (2S)-5-[5-[{2-[3,5-bis(trifluoromethyl)phenyl]-2-methylpropanoyl}(methyl)amino]-4-(4-fluoro-2-methylphenyl)-2-pyridinyl]-2-({[(1,1-dimethylethyl)oxy]carbonyl}amino)-4-pentynoate (Intermediate 2, 750 mg, 1.036 mmol) in dry Dichloromethane (10 ml) trifluoroacetic acid (3 ml, 1.036 mmol) was added and the reaction mixture was stirred for 1 h at r.t. The solvent and the excess of trifluoroacetic acid were removed under vacuum and the residue was purified by SPE-SCX cartridge (10 g). The obtained light yellow solid was dissolved in acetonitrile (10 ml) and AgOTf (26.6 mg, 0.104 mmol) was added and the reaction mixture was stirred overnight at r.t. The solvent was evaporated and the residue was dissolved in ethyl acetate and filtered. The organic layer was collected and evaporated to afford the title compound (645 mg, 1.034 mmol, 100% yield) as a pale yellow solid. UPLC: Rt 0.95 min, m/z 624 [M+H]$^+$.

Intermediates 4 and 5 methyl (5S)-5-[5-[{2-[3,5-bis(trifluoromethyl)phenyl]-2-methylpropanoyl}(methyl)amino]-4-(4-fluoro-2-methylphenyl)-2-pyridinyl]-L-prolinate (4) and methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-L-prolinate (5)

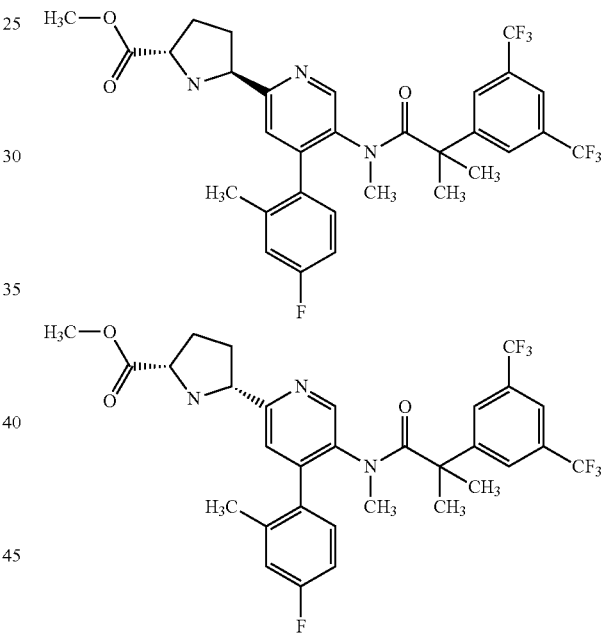

To a solution of methyl (2S)-5-[5-[{2-[3,5-bis(trifluoromethyl)phenyl]-2-methylpropanoyl}(methyl)amino]-4-(4-fluoro-2-methylphenyl)-2-pyridinyl]-3,4-dihydro-2H-pyrrole-2-carboxylate (Intermediate 3, 640 mg, 1.026 mmol) in methanol (10 ml) at 0° C. sodium borohydride (40.8 mg, 1.078 mmol) was added and the reaction mixture was stirred for 2 hours at the same temperature. The reaction was quenched with NaHCO$_3$ 5% solution (1 ml) and the solvent was evaporated. The residue was diluted with water (20 ml) and extracted with ethyl acetate (3×50 ml). The organic layer was dried (Na$_2$SO$_4$), filtered and evaporated and the residue was purified by flash chromatography (Biotage system) on silica gel using a column 40+M and cyclohexane/ethyl acetate 7:3 to ethyl acetate 100% as eluent.

Two products were isolated:

(1st eluted) (Intermediate 4): methyl (5S)-5-[5-[{2-[3,5-bis(trifluoromethyl)phenyl]-2-methylpropanoyl}(methyl)amino]-4-(4-fluoro-2-methylphenyl)-2-pyridinyl]-prolinate (160 mg, 0.256 mmol, 24.92% yield) as a white solid $^1$H NMR (500 MHz, DMSO-d$_6$) δ (ppm): 8.30 (s, 1H) 8.03 (s, 1H) 7.75 (br. s., 2H) 7.39 (s, 1H) 7.17 (d, 1H) 7.10 (br. s., 1H) 7.06 (br. s., 1H) 4.37-4.46 (m, 1H) 3.91-3.99 (m, 1H) 3.64 (s, 3H) 2.29 (br. s., 3H) 2.18-2.24 (m, 1H) 2.08-2.13 (m, 1H) 2.10 (br. s., 3H) 1.80-1.91 (m, 1H) 1.74 (br. s., 1H) 1.50 (br. s., 3H) 1.36 (br. s., 3H), the relative stereochemistry was determined by ROESY (dipolar correlation: H-11 to H-2, H-5; H-2 to H-11, H-3, -3', -4'; H-5 to H-11, H-3', -4, -4'). The atom numbering shown in the following structure is included for the purpose of correlation with the NMR data only. UPLC: Rt 0.81 min (broad signal), m/z 626 [M+H]$^+$.

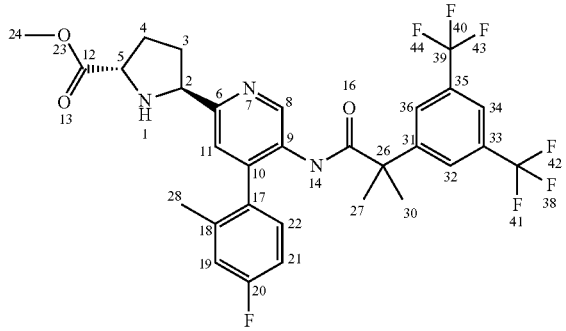 [SMILES: COC(=O)[C@@H]1CC[C@@H](c2cc(-c3ccc(F)cc3C)c(NC(=O)C(C)(C)c3cc(C(F)(F)F)cc(C(F)(F)F)c3)cn2)N1]

(2nd eluted) (Intermediate 5): methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-L-prolinate (220 mg, 0.352 mmol, 34.3% yield) as a white solid. $^1$H NMR (500 MHz, DMSO-d$_6$) δ(ppm): 8.30 (s, 1H) 8.03 (s, 1H) 7.76 (br. s., 2H) 7.57 (br. s., 1H) 7.19 (d, 1H) 7.11 (s, 1H) 7.09 (br. s., 1H) 4.26-4.36 (m, 1H) 3.83-3.92 (m, 1H) 3.60 (s, 3H) 2.27 (br. s., 3H) 2.15-2.23 (m, 1H) 2.06-2.11 (m, 1H) 2.08 (br. s., 3H) 1.84 (br. s., 1H) 1.66-1.75 (m, 1H) 1.51 (br. s., 3H) 1.36 (br. s., 3H), the relative stereochemistry was determined by ROESY (dipolar correlation: H-13 to H-5; H-5 to H-13, H-2, H-3, -4, -4'; H-2 to H-5, H-3, -3',4). The atom numbering shown in the following structure is included for the purpose of correlation with the NMR data only. UPLC: Rt 0.79 min (broad signal), m/z 626 [M+H]$^+$.

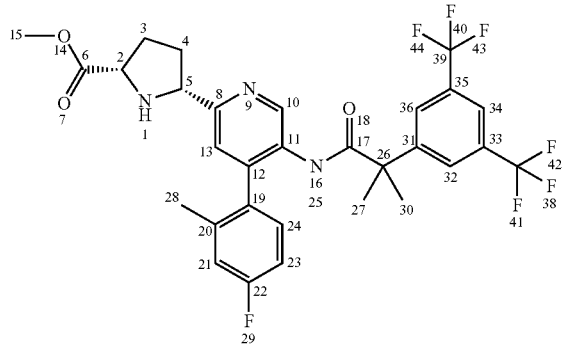 [SMILES: COC(=O)[C@@H]1CC[C@H](c2cc(-c3ccc(F)cc3C)c(NC(=O)C(C)(C)c3cc(C(F)(F)F)cc(C(F)(F)F)c3)cn2)N1]

Intermediate 6

1-(1,1-dimethylethyl) 2-methyl (2S,5R)-5-[4-[{2-[3,5-bis(trifluoromethyl)phenyl]-2-methylpropanoyl}(methyl)amino]-4-(4-fluoro-2-methylphenyl)-2-pyridinyl]1,2-pyrrolidinedicarboxylate

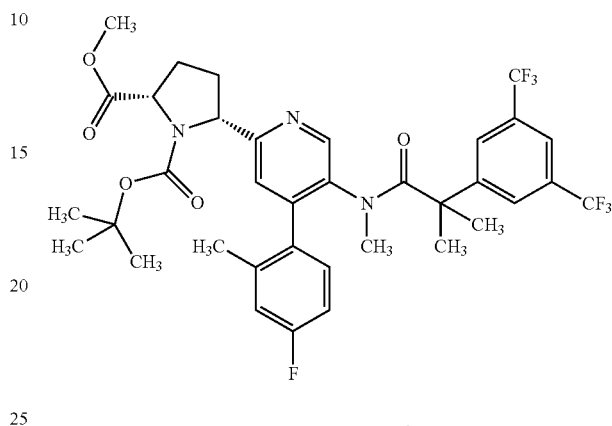

To a solution of methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-prolinate (Intermediate 5, 490 mg, 0.783 mmol) in DCM (10 ml) was added Di-tert-butyl dicarbonate (0.200 ml, 0.862 mmol) and the reaction mixture was stirred for 1 h at r.t. The solvent was evaporated and the residue was purified by flash chromatography on silica gel (Biotage system; eluent: from 1:0 to 1:1 Cyclohexane/Ethyl acetate; 25M cartridge) affording the title compound (525 mg, 0.723 mmol, 92% yield) as a white solid. 1H NMR (400 MHz, DMSO-d$_6$) δ ppm 8.19-8.45 (m, 1H) 7.94-8.11 (m, 1H) 7.54-7.93 (m, 3H) 6.84-7.30 (m, 3H) 4.73-5.08 (m, 1H) 4.23-4.46 (m, 1H) 3.47-3.75 (m, 3H) 0.69-3.40 (m, 25H). UPLC: Rt 1.03 min, m/z 726 [M+H]$^+$.

Intermediates 7 and 8

1-(1,1-dimethylethyl) 2-methyl (2R,5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (7) and 1-(1,1-dimethylethyl) 2-methyl (2S,5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (8)

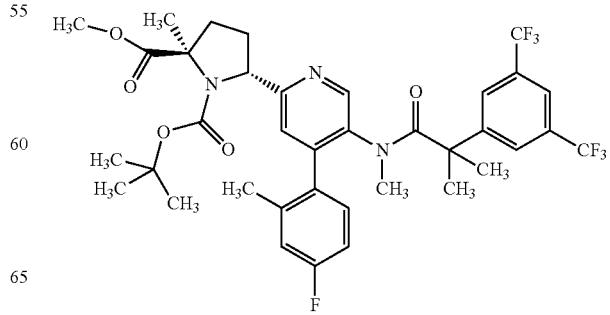

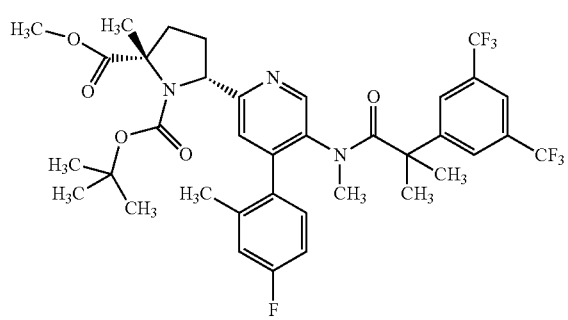

To a solution of 1-(1,1-dimethylethyl) 2-methyl (2S,5R)-5-[5-[{2-[3,5-bis(trifluoromethyl)phenyl]-2-methylpropanoyl}(methyl)amino]-4-(4-fluoro-2-methylphenyl)-2-pyridinyl]-1,2-pyrrolidinedicarboxylate (Intermediate 6, 300 mg, 0.413 mmol) in dry THF (5 ml) was added, at −78° C., 1M Lithium bis(trimethylsilyl)amide solution in THF (0.496 ml, 0.496 mmol) and the reaction mixture was stirred for 10 mins at r.t. Iodomethane (0.103 ml, 1.65 mmol) was added and the reaction mixture was stirred for 30 mins at r.t. The reaction was quenched with brine (1 ml), diluted with water (10 ml) and extracted with ethyl acetate (3×30 ml). The combined organic layers were dried (Na$_2$SO$_4$), filtered and evaporated and the residue was purified by flash chromatography on silica gel (Biotage system; eluent: from 95:5 to 6:4 Cyclohexane/Ethyl acetate; 25M cartridge).

Two compounds were isolated:

(1$^{st}$ eluted) 1-(1,1-dimethylethyl) 2-methyl (2R,5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (Intermediate 7, 31 mg, 0.042 mmol, 10.14% yield) as a white solid. 1H NMR (400 MHz, CHLOROFORM-d) δ ppm 8.29-8.46 (m, 1H) 7.74-7.85 (m, 1H) 7.63-7.75 (m, 2H) 6.84-7.35 (m, 4H) 5.10-5.36 (m, 1H) 3.66-3.87 (m, 3H) 0.75-2.73 (m, 28H). MS: m/z 740 [M+H]+ and 762 [M+Na]+. Chiral analysis, chromatographic conditions: [Column Chiralpak AD-H (25×0.46 cm); mobile phase: n-hexane/2-Propanol 85/15% v/v; Flow rate 1.0 ml/min; DAD 210-340 nm; CD 230 nm] Rt 4.21 min, 94.6% e.e.

(2$^{nd}$ eluted) 1-(1,1-dimethylethyl) 2-methyl (2S,5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (Intermediate 8, 200 mg, 0.27 mmol, 65.4% yield) as a white solid.

1H NMR (400 MHz, CHLOROFORM-d) δ ppm 8.24-8.46 (m, 1H) 7.59-7.98 (m, 4H) 6.77-7.36 (m, 3H) 5.00-5.27 (m, 1H) 3.47-3.75 (m, 3H) 0.83-2.73 (m, 28H). MS: m/z 740 [M+H]$^+$ and 762 [M+Na]$^+$.

Intermediate 9 methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinate

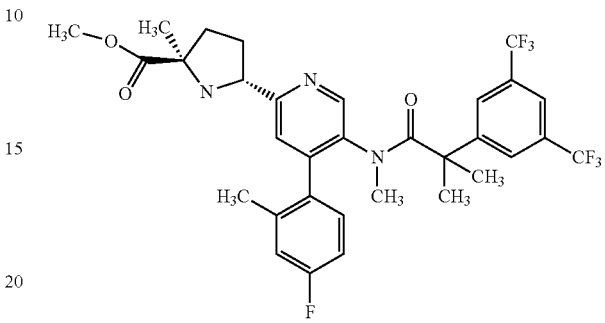

To a solution of 1-(1,1-dimethylethyl) 2-methyl (2R,5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (Intermediate 7, 30 mg, 0.041 mmol) in dry Dichloromethane (2 ml) was added TFA (0.6 ml, 7.79 mmol) and the reaction mixture was stirred for 2 hours at r.t. The solvent and the excess of TFA were evaporated and the residue was purified by SPE-SCX cartridge affording the title compound (25 mg, 0.039 mmol, 96% yield) as a white solid. HPLC: Rt 5.68 min. MS: m/z 640 [M+H]$^+$.

Intermediate 10 methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-L-prolinate

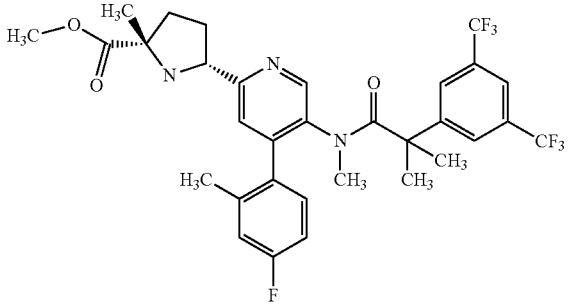 [SMILES: COC(=O)[C@]1(C)CC[C@H](c2cc(-c3ccc(F)cc3C)c(N(C)C(=O)C(C)(C)c3cc(C(F)(F)F)cc(C(F)(F)F)c3)cn2)N1]

To a solution of 1-(1,1-dimethylethyl) 2-methyl (2S,5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (Intermediate 8, 50 mg, 0.068 mmol) in dry Dichloromethane (3 ml) was added TFA (1 ml, 12.98 mmol) and the reaction mixture was stirred for 2 hours at r.t. The solvent and the excess of TFA were evaporated and the residue was purified by SPE-SCX cartridge affording the title compound (42 mg, 0.066 mmol, 97% yield) as a white solid. HPLC: Rt 5.79 min. MS: m/z 640 [M+H]$^+$ and 662 [M+Na]$^+$.

Intermediate 11 methyl (2R)-2-({[(1,1-dimethylethyl)oxy]carbonyl}amino)-4-pentynoate

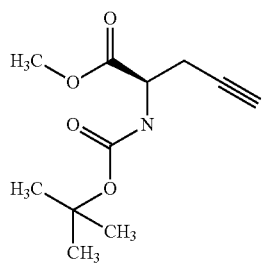 [SMILES: C#CC[C@@H](NC(=O)OC(C)(C)C)C(=O)OC]

To a solution of (2R)-2-amino-4-pentynoic acid (5 g, 44.2 mmol) in Methanol (100 ml) thionyl chloride (15.00 ml, 206 mmol) was added dropwise, at 0° C. and the reaction mixture was stirred overnight at r.t. The solvent and the excess of thionyl chloride were evaporated and the residue was dissolved in 1,4-Dioxane (75 ml) and NaHCO3 sat. sol. (50 ml); a solution of BOC-Anhydride (10.78 ml, 46.4 mmol) in dioxane (10 ml) was added dropwise and the reaction mixture was stirred for 3 hours at r.t. The mixture was extracted with ethyl acetate (3×100 ml). The combined organic layers were dried (Na$_2$SO$_4$), filtered and evaporated to afford the title compound (10 g, 44.0 mmol, 100% yield) as a colourless oil.
$^1$H NMR (400 MHz, CDCl$_3$) δ(ppm): 5.35 (m, 1H), 4.52 (m, 1H), 3.79 (s, 3H), 2.75 (m, 2H), 2.05 (s, 1H), 1.47 (s, 9H). Chiral analysis, chromatographic conditions: [Column Chiralcel OJ-H (25×0.46 cm), 5µ; mobile phase: n-hexane/2-propanol 85/15% v/v; Flow rate 1.0 ml/min; DAD 215 nm, CD 225 nm] Rt 6.9 min, 100% e.e.

Intermediate 12 methyl (2R)-5-[5-[{2-[3,5-bis(trifluoromethyl)phenyl]-2-methylpropanoyl}(methyl)amino]-4-(4-fluoro-2-methylphenyl)-2-pyridinyl]-2-({[(1,1-dimethylethyl)oxy]carbonyl}amino)-4-pentynoate

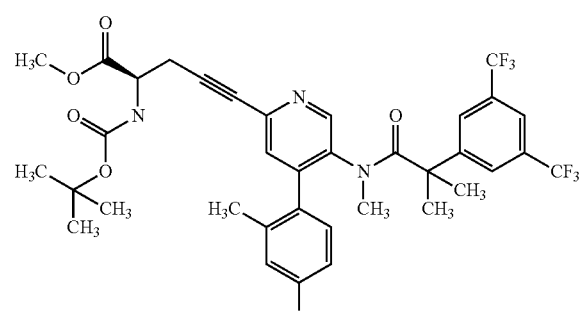

A solution of 2-[3,5-bis(trifluoromethyl)phenyl]-N-[6-chloro-4-(4-fluoro-2-methylphenyl)-3-pyridinyl]-N,2-dimethylpropanamide (WO2005/002577, 1.05 g, 1.97 mmol), methyl (2R)-2-({[(1,1-dimethylethyl)oxy]carbonyl}amino)-4-pentynoate (Intermediate 11, 1.343 g, 5.91 mmol), Pd(PPh$_3$)$_2$Cl$_2$ (69 mg, 0.098 mmol), copper(I) iodide (19 mg, 0.100 mmol) and triphenylphoshine (52 mg, 0.198 mmol) in triethylamine (2 ml)/diisopropylamine (8 ml) was heated at 100° C. under microwave irradiation for 30 min. This reaction was carried out three times always using the amounts of reagents reported above. The reaction mixtures were combined and evaporated to dryness. The final reaction crude was taken-up in water (50 ml) and extracted with DCM (3×50 ml). The organic phases were collected, dried over sodium sulphate and concentrated. Purification on Si (SP1, 65M column) with Cyclohexane/EtOAc [from Cyclohexane 100 to Cyclohexane/EtOAc 70/30 in 4CV and then Cyclohexane/EtOAc 70/30] elution afforded the title compound (2.4 g, 3.32 mmol, 56.1% yield) as a yellow-brown solid. UPLC: Rt 1.02 min, m/z 724 [M+H$^+$]. Chiral analysis, chromatographic conditions: [Column Chiralpak AD-H (25×0.46 cm); mobile phase: n-hexane/Ethanol 70/30% v/v; Flow rate 0.8 ml/min; DAD 210-340 nm, CD 250] Rt 13.43 min, 99.2% e.e.

Intermediate 13 methyl (2R)-2-amino-5-[5-[{2-[3,5-bis(trifluoromethyl)phenyl]-2-methylpropanoyl}(methyl)amino]-4-(4-fluoro-2-methylphenyl)-2-pyridinyl]-4-pentynoate

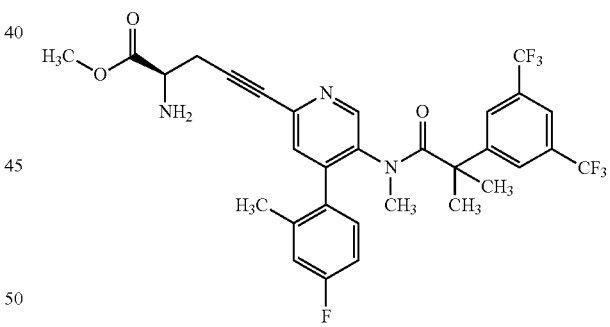

Trifluoroacetic acid (15 ml) was added dropwise to an ice-cooled solution of methyl (2R)-5-[5-[{2-[3,5-bis(trifluoromethyl)phenyl]-2-methylpropanoyl}(methyl)amino]-4-(4-fluoro-2-methylphenyl)-2-pyridinyl]-2-({[(1,1-dimethylethyl)oxy]carbonyl}amino)-4-pentynoate (Intermediate 12, 2.4 g, 3.32 mmol) in anhydrous Dichloromethane (45 ml) and the resulting reaction mixture was stirred at room temperature for 1 h. Volatiles were evaporated. The reaction crude was taken-up in saturated NaHCO$_3$ aqueous solution [until pH=7] (30 ml) and extracted with DCM (2×50 ml). The organic layers were collected, dried over sodium sulphate, filtered and evaporated to obtain the title compound (1.85 g, 2.97 mmol, 89% yield) as a brown solid. UPLC: Rt 0.78 min, m/z 624 [M+H$^+$].

Intermediate 14 methyl (2R)-5-[5-[{2-[3,5-bis(trifluoromethyl)phenyl]-2-methylpropanoyl}(methyl)amino]-4-(4-fluoro-2-methylphenyl)-2-pyridinyl]-3,4-dihydro-2H-pyrrole-2-carboxylate Method A

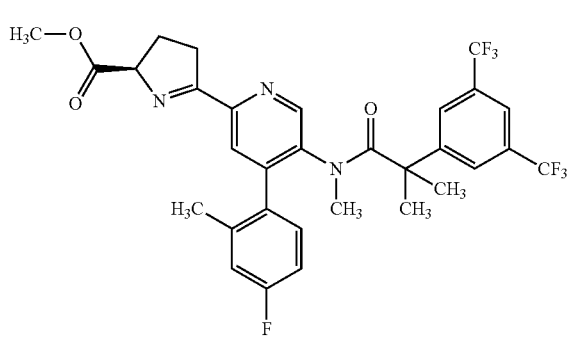 [SMILES: COC(=O)[C@H]1CCC(c2cc(-c3ccc(F)cc3C)c(N(C)C(=O)C(C)(C)c3cc(C(F)(F)F)cc(C(F)(F)F)c3)cn2)=N1]

Silver trifluoromethanesulfonate (0.381 g, 1.483 mmol) was added portionwise to a solution of methyl (2R)-2-amino-5-[5-[{2-[3,5-bis(trifluoromethyl)phenyl]-2-methylpropanoyl}(methyl)amino]-4-(4-fluoro-2-methylphenyl)-2-pyridinyl]-4-pentynoate (Intermediate 13, 1.85 g, 2.97 mmol) in anhydrous Acetonitrile (25 ml) and the resulting reaction mixture was stirred at room temperature overnight. Volatiles were evaporated under vacuo at room temperature. The residue was taken-up in dichloromethane and filtered through a plug of celite to afford 2.2 g of the title compound as a brown solid (the material contained some residual acetonitrile, therefore overall recovered amount was higher than the theoretical amount).

UPLC: Rt 0.95 min, m/z 624 [M+H⁺].

Method B

To a solution of methyl (2R)-5-[5-[{2-[3,5-bis(trifluoromethyl)phenyl]-2-methylpropanoyl}(methyl)amino]-4-(4-fluoro-2-methylphenyl)-2-pyridinyl]-2-({[(1,1-dimethylethyl)oxy]carbonyl}amino)-4-pentynoate (Intermediate 12, 1 g, 1.382 mmol) in Dichloromethane (15 ml), TFA (5 ml, 64.9 mmol) was added and the reaction mixture was stirred for 1 h at r.t. The solvent and the excess of TFA were evaporated and the residue purified by SPE-SCX cartridge to obtain Intermediate 13. This residue was dissolved in Acetonitrile (14 ml) and Silver trifluoromethanesulfonate (0.036 g, 0.138 mmol) was added; the reaction mixture was stirred for 6 hours at 60° C. The solvent was evaporated and the residue was dissolved in DCM (15 ml) and the metal catalyst was filtered off. The organic solution was evaporated affording the title compound (800 mg, 1.283 mmol, 93% yield) as an orange solid. UPLC: Rt 0.95 min, m/z 624 [M+H⁺].

Intermediates 15 and 16 methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-D-prolinate (15) and methyl (5S)-5-[5-[{2-[3,5-bis(trifluoromethyl)phenyl]-2-methylpropanoyl}(methyl)amino]-4-(4-fluoro-2-methylphenyl)-2-pyridinyl]-D-prolinate (16)

Method A

To a solution of methyl (2R)-5-[5-[{2-[3,5-bis(trifluoromethyl)phenyl]-2-methylpropanoyl}(methyl)amino]-4-(4-fluoro-2-methylphenyl)-2-pyridinyl]-3,4-dihydro-2H-pyrrole-2-carboxylate (Intermediate 14 from Method A, 1.3 g, 2.085 mmol) in THF (20.85 ml) at −40° C., 1M BH₃.THF solution in THF (6.25 ml, 6.25 mmol) was slowly added and the reaction mixture was stirred for 2 hours at the same temperature. The reaction was quenched with MeOH (2 ml) and stirred at r.t. for 2 hours. The solution was diluted with Brine (50 ml) and extracted with ethyl acetate (3×80 ml). The organic layer was dried (Na₂SO₄), filtered and evaporated and the residue was purified by flash chromatography (Biotage system) on silica gel using a column 40+M and cyclohexane/ethyl acetate 7:3 to ethyl acetate as eluent to obtain two compounds:

(first eluted) (Intermediate 15) methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-D-prolinate (350 mg, 0.559 mmol, 26.8% yield) ¹H NMR (400 MHz, DMSO-d₆) δ(ppm): 8.30 (s, 1H), 8.03 (s, 1H), 7.75 (br.s, 2H), 7.39 (s, 1H), 7.17 (d, 1H), 7.10 (br.s, 1H), 7.06 (br.s, 1H), 4.37-4.46 (m, 1H), 3.91-3.99 (m, 1H), 3.64 (s, 3H), 2.29 (br.s, 3H), 2.18-2.24 (m, 1H), 2.08-2.13 (m, 1H), 2.10 (br.s., 3H), 1.80-1.91 (m, 1H), 1.68-1.81 (br.s, 1H), 1.50 (br.s., 3H), 1.36 (br.s, 3H). The relative stereochemistry was assigned by comparison with the NMR spectrum of the corresponding enantiomer (Intermediate 4), UPLC: Rt 0.76 min (broad signal), m/z 626 [M+H]+.

(second eluted) (Intermediate 16) methyl (5S)-5-[5-[{2-[3,5-bis(trifluoromethyl)phenyl]-2-methylpropanoyl}(methyl)amino]-4-(4-fluoro-2-methylphenyl)-2-pyridinyl]-D-prolinate (355 mg, 0.567 mmol, 27.2% yield).

1H NMR (500 MHz, DMSO-d6) δ(ppm): 8.30 (s, 1H), 8.03 (s, 1H), 7.76 (br.s, 2H), 7.57 (br.s, 1H), 7.19 (d, 1H), 6.92-7.26 (m, 2H), 4.26-4.36 (m, 1H), 3.83-3.92 (m, 1H), 3.60 (s, 3H), 2.20-2.36 (m, 3H), 2.15-2.24 (m, 1H), 2.03-2.16 (m, 4H), 1.79-1.90 (m, 1H), 1.66-1.76 (m, 1H), 1.12-1.57 (m, 6H). The relative stereochemistry was assigned by comparison with the NMR spectrum of the corresponding enantiomer (Intermediate 5), UPLC: Rt 0.78 min (broad signal), m/z 626 [M+H]+.

Method B

To a solution of methyl (2R)-5-[5-[{2-[3,5-bis(trifluoromethyl)phenyl]-2-methylpropanoyl}(methyl)amino]-4-(4-fluoro-2-methylphenyl)-2-pyridinyl]-3,4-dihydro-2H-pyrrole-2-carboxylate (Intermediate 14 from Method B, 650 mg, 1.042 mmol) in Methanol (10 ml) at 0° C. sodium borohydride (43.4 mg, 1.147 mmol) was added and the reaction mixture was stirred for 2 hours at the same temperature. The reaction was quenched with NaHCO3 5% solution (1 ml) and the solvent was evaporated. The residue was diluted with water (20 ml) and extracted with ethyl acetate (3×50 ml). The organic layer was dried (Na2SO4), filtered and evaporated and the residue was purified by flash chromatography (Biotage system) on silica gel using a column 40+M and 7:3 Cyclohexane/ethyl acetate to ethyl acetate as eluent. Two different products were isolated:

(first eluted) (Intermediate 15) methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-D-prolinate (100 mg, 0.160 mmol, 15.34% yield) as a white solid, (second eluted) (Intermediate 16) methyl (5S)-5-[5-[{2-[3,5-bis(trifluoromethyl)phenyl]-2-methylpropanoyl}(methyl)amino]-4-(4-fluoro-2-methylphenyl)-2-pyridinyl]-D-prolinate (160 mg, 0.256 mmol, 24.54% yield) as a white solid.

Intermediate 17

1-(1,1-dimethylethyl) 2-methyl (2R,5S)-5-[5-[{2-[3,5-bis(trifluoromethyl)phenyl]-2-methylpropanoyl}(methyl)amino]-4-(4-fluoro-2-methylphenyl)-2-pyridinyl]-1,2-pyrrolidinedicarboxylate

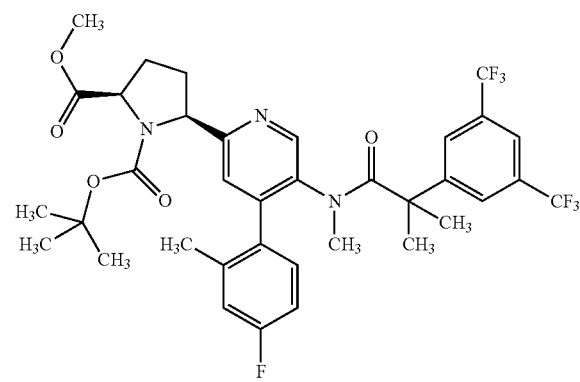 [SMILES: COC(=O)[C@H]1CC[C@@H](c2cc(-c3ccc(F)cc3C)c(N(C)C(=O)C(C)(C)c3cc(C(F)(F)F)cc(C(F)(F)F)c3)cn2)N1C(=O)OC(C)(C)C]

To a solution of methyl (5S)-5-[5-[{2-[3,5-bis(trifluoromethyl)phenyl]-2-methylpropanoyl}(methyl)amino]-4-(4-fluoro-2-methylphenyl)-2-Pyridinyl]-D-Prolinate (intermediate 16, 700 mg, 1.119 mmol) in dry Dichloromethane (DCM) (11 ml) was added Di-tert-butyl dicarbonate (0.286 ml, 1.231 mmol) and the reaction mixture was stirred for 1 h at r.t. The solvent was evaporated and the residue was purified by flash chromatography on silica gel (Biotage system; eluent from 1:0 to 1:1 Cyclohexane/Ethyl acetate; 25M cartridge) affording the title compound (512 mg, 0.706 mmol, 63.1% yield) as a white solid. UPLC: Rt 1.03 min, m/z 726 [M+H]+.

Intermediates 18 and 19

1-(1,1-dimethylethyl) 2-methyl (2S,5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (18) and 1-(1,1-dimethylethyl) 2-methyl (2R,5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (19)

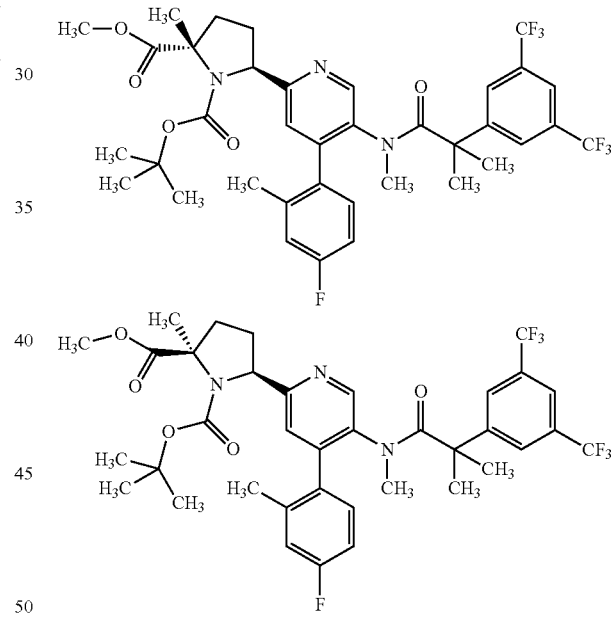

To a solution of 1-(1,1-dimethylethyl) 2-methyl (2R,5S)-5-[5-[{2-[3,5-bis(trifluoromethyl)phenyl]-2-methylpropanoyl}(methyl)amino]-4-(4-fluoro-2-methylphenyl)-2-pyridinyl]-1,2-pyrrolidinedicarboxylate (intermediate 17, 150 mg, 0.207 mmol) in dry Tetrahydrofuran (THF) (2 ml) was added, at −78° C., 1M Lithium bis(trimethylsilyl)amide solution in hexanes (0.248 ml, 0.248 mmol) and the reaction mixture was stirred for 30 mins at −30° C. The reaction mixture was then cooled to −78° C., Iodomethane (0.019 ml, 0.31 mmol) was added and the resulting reaction mixture was stirred for 1 h at the same temperature. The reaction was quenched with brine (1 ml), diluted with water (4 ml) and extracted with ethyl acetate (2×10 ml). The combined organic layers were dried (Na2SO4), filtered and evaporated and the residue was purified by flash chromatography on silica gel (Biotage system; eluent: from 1:0 to 6:4 Cyclohexane/Ethyl acetate; 12M cartridge). Two different diastereoisomers were isolated:

(1st eluted) 1-(1,1-dimethylethyl) 2-methyl (2S,5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (Intermediate 18, 7 mg, 9.46 μmol, 4.58% yield). UPLC: Rt 1.09 min, m/z 740 [M+H]+.

(2nd eluted) 1-(1,1-dimethylethyl) 2-methyl (2R,5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (Intermediate 19, 70 mg, 0.095 mmol, 45.8% yield). UPLC: Rt 1.06 min, m/z 740 [M+H]+.

Intermediate 20 methyl (5S)-5-[5-[{2-[3,5-bis(trifluoromethyl)phenyl]-2-methylpropanoyl}(methyl)-amino]-4-(4-fluoro-2-methylphenyl)-2-pyridinyl]-2-methyl-D-prolinate

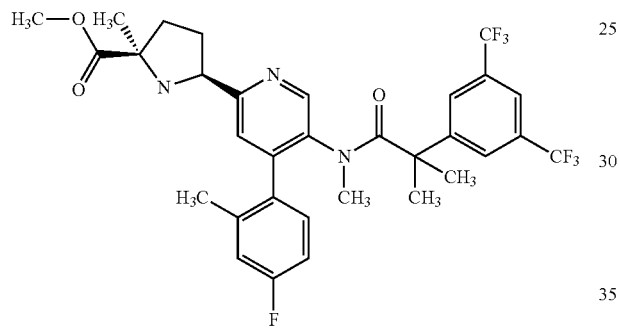

To a solution of 1-(1,1-dimethylethyl) 2-methyl (2R,5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-1,2-pyrrolidinedicarboxylate (Intermediate 19, 70 mg, 0.095 mmol) in dry Dichloromethane (DCM) (2 ml) was added TFA (0.5 ml, 6.49 mmol) and the reaction mixture was stirred for 2.5 hours at r.t. The solvent and the excess of TFA were evaporated and the residue was purified by SPE-SCX cartridge to afford the title compound (55 mg, 0.086 mmol, 91% yield) as a white solid. UPLC: Rt 0.76 min (broad peak), m/z 640 [M+H]+.

Intermediate 21 methyl (2R)-2-[(tert-butoxycarbonyl)amino]-2-methylpent-4-ynoate

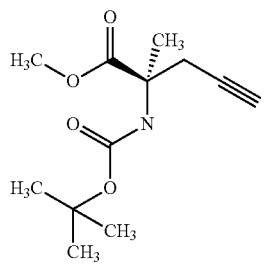 [SMILES: C#CC[C@@](C)(NC(=O)OC(C)(C)C)C(=O)OC]

(2R)-2-amino-2-methylpent-4-ynoic acid (1.3 kg) was suspended in methanol (6.5 L) and cooled to 2±3° C. The mixture was treated with thionyl chloride (1.48 L) at 2±3° C. over at least 30 mins. The mixture was heated at 40±3° C. for at least 17 hours then sampled for completion of reaction (COR) by 1H NMR. Once complete, the mixture was stripped to low volume (ca. 1 vol) then azeotroped with toluene (ca. 2×2.5 L) and evaporated to dryness to afford crude methyl (2R)-2-amino-2-methylpent-4-ynoate which was then diluted with dioxane (9.1 L). The suspension was treated with aqueous potassium carbonate (2.82 Kg dissolved in 5.46 L of water) at ambient temperature and stirred for at least 30 minutes. Di-tert butyl dicarbonate (BOC2O) (2.43 Kg) was then added and the mixture heated at 40±3° C. with stirring under inert atmosphere for at least 17 hours. The mixture was sampled for completion of reaction (COR) by 1H NMR Once complete the mixture was filtered to remove solids then diluted with ethyl acetate (5 L), stirred and separated. The organic layer was washed with water (5 L) then the organic layer separated and dried over anhydrous sodium sulphate. The solution was then concentrated to a clear oil which crystallized upon standing. The crude product was recrystallised from cyclohexane (2.6 L) and washed with further cyclohexane (2.6 L). The product was dried in vacuo at 35° C. to furnish the title compound (1.5 Kg.). 1H NMR (400 MHz, MeOD-d4) δppm: 1.42 (9H, s), 1.46 (3H, s), 2.32-2.34 (1H, m), 2.65-2.71 (1H, dd), 2.92-2.99 (1H, d), 3.70 (3H, s).

Intermediate 22 methyl (2R)-5-[5-[{2-[3,5-bis(trifluoromethyl)phenyl]-2-methylpropanoyl}(methyl)amino]-4-(4-fluoro-2-methylphenyl)pyridin-2-yl]-2-[(tert-butoxycarbonyl)amino]-2-methylpent-4-ynoate

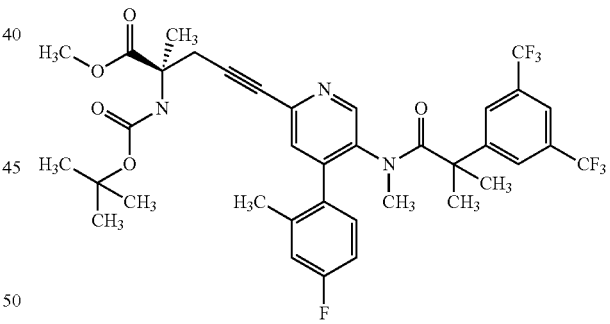

(750 g) of 2-[3,5-bis(trifluoromethyl)phenyl]-N-[6-chloro-4-(4-fluoro-2-methylphenyl)pyridin-3-yl]-N,2-dimethylpropanamide (WO2005/002577 intermediate 4D), PdCl2(Ph3P)2 (19.8 g), CuI (5.4 g), Ph3P (14.8 g) in 4:1 diisopropylamine:triethylamine (3.75 L) were charged to flask and heated to reflux. Intermediate 21 (441.2 g) in 4:1 diisopropylamine:triethylamine (3.7 L) was added slowly over 7-8 hours. The mixture was heated for a further 14-18 hours until intermediate 21 is consumed. The mixture was filtered hot to remove the iPr2NH.HCl and washed with 4:1 diisopropylamine:triethylamine (0.75 L). The solid was washed with n-heptane (3.75 L) and the mixture cooled to room temperature. When crystallization had occurred the mixture was diluted with n-heptane (7.5 L) and stirred for a further 1 hour. The solid was filtered and washed with n-heptane (3.75 L). The solids was dried at 40° C. under vacuum to give the title compound (839.1 g).

¹H NMR (500 MHz, DMSO-d6) δppm: 1.36-1.45 (18H, m), 2.12 (3H, s), 2.86-2.91 (1H, d), 3.18-3.24 (1H, br. d.), 3.64 (3H, s), 7.09-7.19 (3H, m), 7.41 (1H, s), 7.75 (2H, s) 8.01 (1H, s), 8.37 (1H, s).

Intermediate 23 methyl (2R)-5-[5-[{2-[3,5-bis(trifluoromethyl)phenyl]-2-methylpropanoyl}(methyl)amino]-4-(4-fluoro-2-methylphenyl)pyridin-2-yl]-2-methyl-3,4-dihydro-2H-pyrrole-2-carboxylate

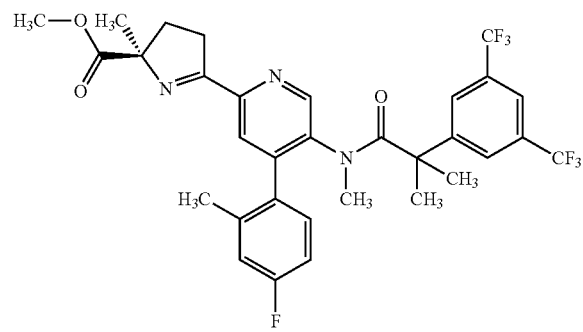 [SMILES: COC(=O)[C@@]1(C)CCC(c2cc(-c3ccc(F)cc3C)c(N(C)C(=O)C(C)(C)c3cc(C(F)(F)F)cc(C(F)(F)F)c3)cn2)=N1]

Methyl (2R)-5-[5-[{2-[3,5-bis(trifluoromethyl)phenyl]-2-methylpropanoyl}(methyl)amino]-4-(4-fluoro-2-methylphenyl)pyridin-2-yl]-2-[(tert-butoxycarbonyl)amino]-2-methylpent-4-ynoate (Intermediate 22, 1.23 Kg) was suspended in 6.2 L DCM at room temperature under inert atmosphere. The mixture was then heated to reflux (clear solution obtained at 30° C.). TFA (990 ml) was added dropwise over one hour. The resulting solution was stirred for at least 6 h at reflux and then was cooled to 20° C.±5° C. Water (6.15 L) was added and the biphasic mixture was stirred for 15 min. Layers were separated and the aqueous layer (top) was discarded. 6.1 L 10% w/w aqueous potassium carbonate was added to the DCM layer and the biphasic mixture was stirred for 15 min. Layers were separated and the top layer (aqueous) was discarded. The DCM layer was dried over magnesium sulfate and was filtered. Acetonitrile (620 ml) was added to the above DCM solution and silver triflate (128.4 g,) was also charged to the vessel. The resulting mixture was then heated to reflux and stirred for 24 h. It was then cooled to 20° C. and quenched with 8.6 L. saturated ammonium chloride. The mixture was stirred for 1 h at 20° C. and was then cooled to 0° C. and stirred for 1 h. The silver chloride precipitate was then filtered cold and the resulting biphasic solution was allowed to warm to 20° C. Layers were separated. The top aqueous layer was discarded. The organic layer was dried over magnesium sulfate, filtered and evaporated to dryness under vacuum to give the title compound (1067.6 g).

¹H NMR (500 MHz, 333K, DMSO-d6) δppm: 1.42 (6H, br. s.), 1.47 (3H, s), 1.90-1.96 (1H, m), 2.11 (3H, s), 2.36-2.44 (1H, m), 2.52 (3H, s), 3.18-3.25 (3H, m), 3.65 (3H, s), 7.05-7.10 (1H, m), 7.13-7.19 (2H, m), 7.77 (2H, s), 7.90 (1H, s), 7.99 (1H, s), 8.49 (1H, s).

Intermediate 24

(2R)-5-[5-[{2-[3,5-bis(trifluoromethyl)phenyl]-2-methylpropanoyl}(methyl)amino]-4-(4-fluoro-2-methylphenyl)pyridin-2-yl]-2-methyl-3,4-dihydro-2H-pyrrole-2-carboxamide

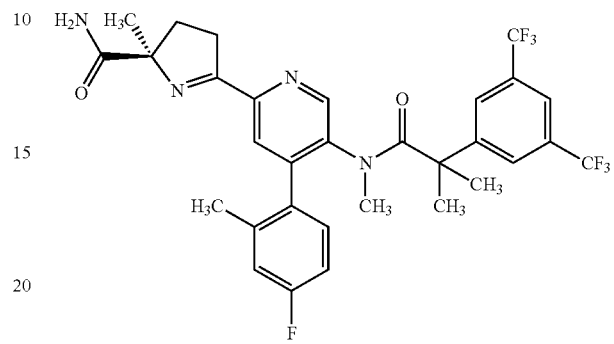

Methyl (2R)-5-[5-[{2-[3,5-bis(trifluoromethyl)phenyl]-2-methylpropanoyl}(methyl)amino]-4-(4-fluoro-2-methylphenyl)pyridin-2-yl]-2-methyl-3,4-dihydro-2H-pyrrole-2-carboxylate (Intermediate 23 1.06 Kg) was suspended in 20.44 L of 7M ammonia in methanol. The mixture was gently stirred for at least 5 days at 20° C. The mixture was concentrated by half by distillation at atmospheric pressure. The solution obtained was then cooled to 40° C. and stirred for 1 h. The slurry obtained was then cooled to 0° C. over 3 h and aged at 0° C. for 2 h.

The title compound was then isolated by filtration and the cake washed with ice cold methanol (1.1 L). The wet cake was dried at 40° C./vacuum to yield the title compound (841.3 g).

¹H NMR (500 MHz, 333K, DMSO-d6) δppm: 1.39 (3H, s), 1.43 (6H, br. s.), 1.91-1.97 (1H, m), 2.15 (3H, s), 2.21-2.28 (1H, m), 2.53 (3H, s), 3.07-3.20 (2H, m), 6.79-6.94 (2H, br. d.), 7.06-7.11 (1H, br. t.), 7.15-7.20 (2H, m), 7.78 (2H, s), 7.99 (1H, s), 8.14 (1H, s), 8.47 (1H, s).

Example 1

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide

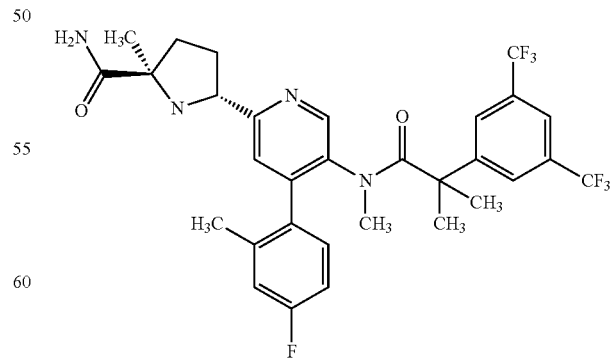

Methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinate (Intermediate 9, 25 mg, 0.039 mmol) was dissolved in 7N ammonia solution in MeOH (3 ml, 21.0 mmol) and the reaction mixture was stirred for 48 hours at 60° C. The solvent was evaporated and the residue was purified by flash chromatography on silica gel (Companion system; eluent: from 99:1 Dichloromethane/MeOH to 95:5 Dichloromethane/MeOH; 12 g cartridge) affording the title compound (16 mg, 0.026 mmol, 65.5% yield) as a white solid.

1H NMR (400 MHz, DMSO-$d_6$) δ ppm 8.32-8.42 (m, 1H) 8.02-8.09 (m, 1H) 7.68-7.87 (m, 2H) 7.50-7.58 (m, 1H) 7.43 (s, 1H) 6.95-7.28 (m, 4H) 4.19-4.38 (m, 1H) 3.04-3.24 (m, 1H) 2.54 (s, 3H) 2.19 (s, 3H) 1.99-2.42 (m, 2H) 1.56-1.87 (m, 2H) 1.37 (s, 3H) 1.42 (s, 6H) The relative stereochemistry anti was assigned by comparison with the NMR spectrum of the syn diastereoisomer (Example 3): the spectra were different. HPLC: Rt 5.49 min. MS: m/z 625 [M+H]$^+$ and 647 [M+Na]$^+$.

Example 2

(5R)-5-[5-[{2-[3,5-bis(trifluoromethyl)phenyl]-2-methylpropanoyl}(methy)amino]-4-(4-fluoro-2-methylphenyl)-2-pyridinyl]-2-methyl-D-prolinamide hydrochloride

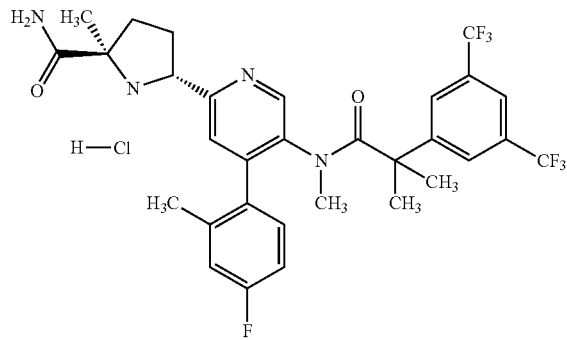 [SMILES: Cc1cc(F)ccc1-c1cc([C@H]2CC[C@](C)(C(N)=O)N2)ncc1N(C)C(=O)C(C)(C)c1cc(C(F)(F)F)cc(C(F)(F)F)c1 ; Cl]

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 1, 16 mg, 0.026 mmol) was dissolved in diethyl ether (2 ml) and 1N HCl in diethyl ether (30 μl) was added. The suspension was triturated to afford the title compound (16 mg, 0.024 mmol, 92% yield) as a white solid. HPLC: Rt 5.46 min. MS: m/z 625 [M+H]$^+$ and 647 [M+Na]$^+$ (free base).

Example 3

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-L-prolinamide

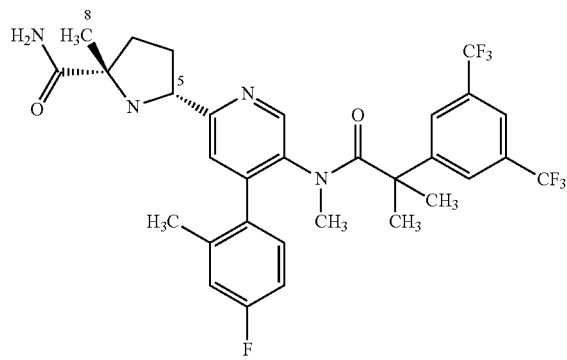 [SMILES: Cc1cc(F)ccc1-c1cc([C@H]2CC[C@@](C)(C(N)=O)N2)ncc1N(C)C(=O)C(C)(C)c1cc(C(F)(F)F)cc(C(F)(F)F)c1]

Methyl (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-L-prolinate (Intermediate 10, 42 mg, 0.066 mmol) was dissolved in 7N ammonia solution in MeOH (3 ml, 21.0 mmol) and the reaction mixture was stirred for 48 hours at 60° C. The solvent was evaporated and the residue was purified by flash chromatography on silica gel (Companion system; eluent: from 99:1 Dichloromethane/MeOH to 95:5 Dichloromethane/MeOH; 12 g cartridge) affording the title compound (28 mg, 0.045 mmol, 68.3% yield) as a white solid. 1H NMR (400 MHz, DMSO-$d_6$) δ ppm 8.31 (s, 1H) 8.04 (s, 1H) 7.89-7.99 (m, 1H) 7.60-7.87 (m, 2H) 7.44 (s, 1H) 6.90-7.24 (m, 4H) 4.39-4.60 (m, 1H) 3.21-3.32 (m, 1H) 2.53 (s, 3H) 2.21 (s, 3H) 1.45 (s, 6H) 1.38 (s, 3H) 1.16-2.37 (m, 4H), The relative stereochemistry syn was confirmed by dipolar correlations between CH$_3$(8) and CH(5). HPLC: Rt 5.48 min. MS: m/z 625 [M+H]$^+$.

Example 4

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-L-prolinamide hydrochloride

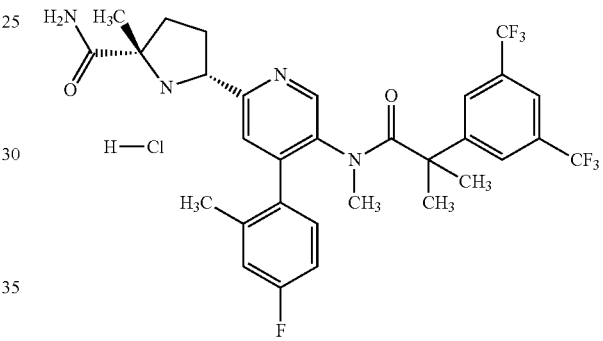

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-L-prolinamide (Example 3, 28 mg, 0.045 mmol) was dissolved in diethyl ether (2 ml) and 1N HCl in diethyl ether (50 μl) was added. The suspension was triturated to afford the title compound (28 mg, 0.042 mmol, 93% yield) as a white solid. HPLC: Rt 5.45 min. MS: m/z 625 [M+H]$^+$ (free base).

Example 5

(5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide

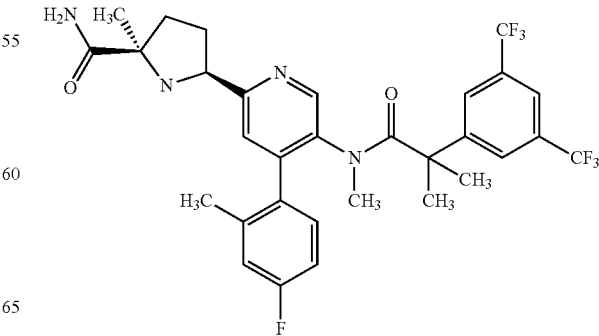

Methyl (5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinate (Intermediate 20, 30 mg, 0.047 mmol) was dissolved in 7N ammonia solution in MeOH (3 ml) and the reaction mixture was stirred for 48 hours at 50° C. The solvent was evaporated affording the title compound (27 mg, 0.043 mmol, 92% yield) as a white solid. 1H NMR (500 MHz, DMSO-$d_6$) δ ppm 8.31 (s, 1H) 8.04 (s, 1H) 7.89-7.99 (m, 1H) 7.60-7.87 (m, 2H) 7.44 (s, 1H) 6.90-7.24 (m, 4H) 4.39-4.60 (m, 1H) 3.21-3.32 (m, 1H) 2.53 (s, 3H) 2.21 (s, 3H) 1.45 (s, 6H) 1.38 (s, 3H) 1.16-2.37 (m, 4H) The spectrum of the sample consists of a mixture of conformers (broad lines in the spectrum at r.t). The relative stereochemistry syn was confirmed by dipolar correlation between: —$CH_3(8)$ at 1.31 ppm and CH(5) at 4.48 ppm. UPLC: Rt 0.75 min (broad peak), m/z 625 [M+H]$^+$. HPLC: Rt 5.06 min.

Example 6

(5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide hydrochloride

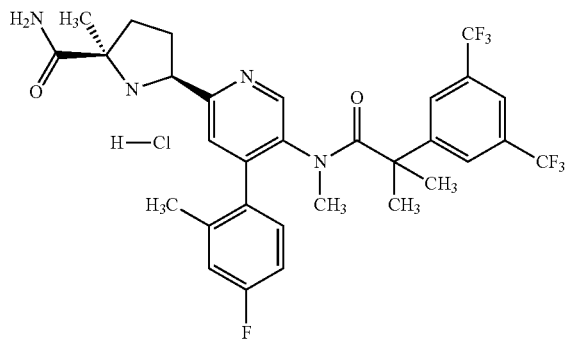

(5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 5, 27 mg, 0.043 mmol) was dissolved in diethyl ether (2 ml) and 1N HCl in diethyl ether was added. The suspension was triturated to afford the title compound (26 mg, 0.039 mmol, 91% yield) as a white solid. UPLC: Rt 0.77 min (broad peak), m/z 625 [M+H]$^+$ (free base). HPLC: Rt 5.18 min.

Example 7

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide anhydrous crystalline Form 1

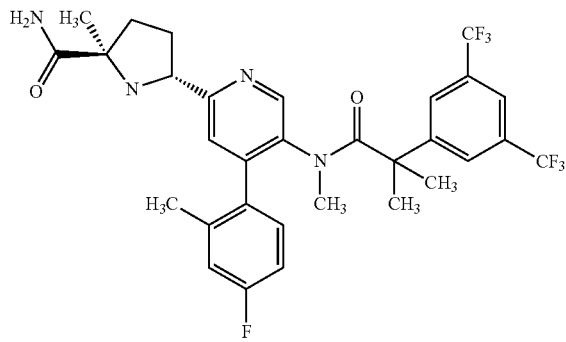 [SMILES: Cc1cc(F)ccc1-c1cc([C@H]2CC[C@](C)(C(N)=O)N2)ncc1N(C)C(=O)C(C)(C)c1cc(C(F)(F)F)cc(C(F)(F)F)c1]

TFA (0.2 L) was added to a stirred solution of (2R)-5-[5-[{2-[3,5-bis(trifluoromethyl)phenyl]-2-methylpropanoyl}(methyl)amino]-4-(4-fluoro-2-methylphenyl)pyridin-2-yl]-2-methyl-3,4-dihydro-2H-pyrrole-2-carboxamide (intermediate 24, 0.82 Kg) in DCM (6.55 L) at room temperature. The resultant solution was cooled to 0° C. Sodium triacetoxy borohydride (0.423 Kg) was added portion-wise and the reaction stirred for 2-4 hr. MeOH (0.4 L) was added to the reaction then water (1.64 L) was added carefully, followed by 3M NaOH (4.0 L) to raise the pH to 12. The layers are separated and the DCM layer retained. The aqueous layer was washed with DCM (0.8 L) and the layers separated. The organic layers were combined and washed with saturated brine solution. The organic layer was dried over magnesium sulphate and concentrated on a rotary evaporator to give (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 1) and 5S)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 5) in approximately mixture of 4:1, as a white foam (859.5 g). To a such mixture (0.8 Kg), TBME (6 L) was added and the resultant solution was filtered. The solution was stirred at room temperature overnight. The resulting suspension was filtered and the cake rinsed with TBME (0.8 L) The damp solid was dried under vacuum to furnish the title compound, in approximately 97% purity as a white crystalline solid (446.4 g.).

This compound (598.8 g) was then suspended in ethyl acetate (1.2 L) at room temperature then heated to reflux. The resultant hot solution was filtered/clarified to remove any particulate matter. Methylcyclohexane (6.0 L) was added slowly at reflux to the filtrate giving rise to a white suspension by the end of the addition. The hot suspension was cooled to 20° C. over 4 hrs and then left at 20° C. stirring overnight. The suspension was filtered and rinsed with methylcyclohexane (1.2 L) then dried undervacuum at 40° C. for 26 hrs to furnish the title compound, in approximately 99% purity, as a white crystalline solid (527 g.)

$^1$H NMR (500 MHz, 353K, DMSO-d6) δppm: 1.40 (3H, s), 1.42 (6H, s), 1.65-1.70 (1H, m), 1.78-1.85 (1H, m), 2.11-2.24 (5H, m) 3.08 (1H, br. s.), 4.31-4.34 (1H, t), 7.03-7.07 (1H, m), 7.13-7.17 (2H, m), 7.37 (1H, s) 7.76 (2H, s), 7.96 (1H, s), 8.32 (1H, s).

Onset melt 198.7° C. by DSC.

The DSC thermogram was obtained using a TA Instruments Q2000 differential scanning calorimeter. The sample was weighed into an aluminium pan, a pan lid placed on top and lightly crimped without sealing the pan. The experiment was conducted using a heating rate of 10° C./min.

Considering 2 theta angles (°) and d-spacing (Å), the compound of Example 7 exhibits the following XRPD pattern characteristics: (Table 1)

TABLE 1

| No. | 2 theta angles (°) | d-spacing [Å] |
|---|---|---|
| 1 | 6.0 | 14.8 |
| 2 | 6.5 | 13.6 |
| 3 | 8.2 | 10.8 |
| 4 | 10.0 | 8.9 |
| 5 | 10.9 | 8.1 |
| 6 | 11.9 | 7.4 |
| 7 | 13.0 | 6.8 |
| 8 | 13.9 | 6.4 |
| 9 | 16.3 | 5.4 |

TABLE 1-continued

| No. | 2 theta angles (°) | d-spacing [Å] |
|---|---|---|
| 10 | 17.0 | 5.2 |
| 11 | 17.9 | 5.0 |
| 12 | 19.1 | 4.7 |
| 13 | 19.5 | 4.6 |
| 14 | 20.0 | 4.4 |
| 15 | 20.2 | 4.4 |
| 16 | 21.0 | 4.2 |
| 17 | 21.9 | 4.1 |
| 18 | 22.1 | 4.0 |
| 19 | 24.6 | 3.6 |
| 20 | 24.9 | 3.6 |
| 21 | 27.9 | 3.2 |
| 22 | 28.2 | 3.2 |
| 23 | 29.9 | 3.0 |
| 24 | 30.4 | 2.9 |
| 25 | 33.1 | 2.7 |

The XRPD pattern of the compound of Example 7 is shown in FIG. 1. The XRPD pattern is expressed in terms of 2 theta angles and obtained with a diffractometer using copper Kα X-radiation, according to the procedures described above (under Experimental).

Example 8

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide tartrate Acetone (7 ml) was added to tartaric acid (126.15 mg, 1 eq) in order to dissolve the acid. The acid solution was then added to 500 mg of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 1). The resulting slurry was set up to temperature cycle (0-40° C.) whilst stirring at 500 rpm. After 1 hour, a thick, gel-like material had formed. Further acetone (13 ml) was then added in order to improve the mobility of the material. The reaction was temperature cycled for a further 3 days whilst stirring. The solid was then isolated and allowed to dry at 45° C. overnight to obtained the title compound in a crystalline form (463 mg). Onset melt 211° C. by DSC.

Example 9

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide benzoate Toluene (3.5 ml) was added to benzoic acid (102.65 mg, 1 eq) in order to dissolve the acid. The acid solution was then added to 500 mg of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 1). After heating to 40° C. and then cooling down to 20° C., the reaction was seeded with benzoate crystals of Example 1 which were obtained through a small scale evaporation experiment (50 mg) from toluene). The reaction was then temperature cycled for 3 days. The solid which formed was isolated and allowed to dry at 45° C. overnight to obtain the title compound (374 mg) as a crystalline form. Onset melt 131° C. by DSC.

Example 10

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide citrate 25 mg of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 1) were dispensed into a HPLC vial followed by 7.6 mg (1 eq) citric acid. 250 µL of toluene were then dispensed on to the solid and the reaction was set to temperature cycle (0-40° C.) whilst stirring at 500 rpm. After 2.5 days, the solid was isolated by filtration at ambient. Onset melt ca. 90° C. by DSC followed by decomposition.

Example 11

(5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide bis-hydrochloride

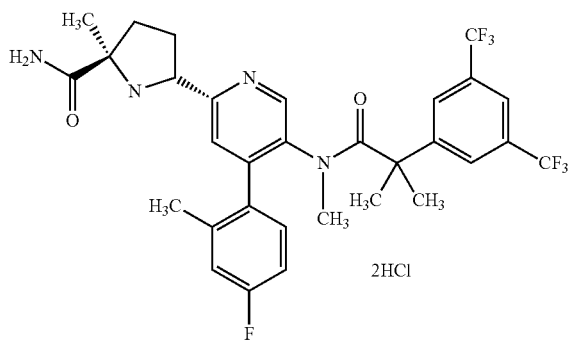

To a solution of (5R)-5-[5-[{2-[3,5-bis(trifluoromethyl)phenyl]-2-methylpropanoyl}(methyl)amino]-4-(4-fluoro-2-methylphenyl)-2-pyridinyl]-2-methyl-D-prolinamide (Example 1 107.45 g, 172 mmol) in dry diethyl ether (1000 mL) cooled to 0° C. hydrochloric acid (1M in Et2O) (353 mL, 353 mmol) was added dropwise in 30 min. The suspension was stirred at 0° C. for 30 min then 1 hr at room temperature.

Volatiles were evaporated under vacuum. Title compound (118.7 g, 99% yield) was recovered as white solid.

HPLC: Rt=5.168 mins.

$^1$H NMR (400 MHz, DMSO-d$_6$) δ ppm 9.43 (br. s., 1H), 9.10 (br. s., 1H), 8.52 (s, 1H), 7.99-8.15 (m, 2H), 7.84 (s, 1H), 7.64-7.89 (m, 2H), 7.54 (s, 1H), 6.96-7.29 (m, 3H), 4.87-5.09 (m, 1H), 2.50 (s, 3H), 2.35 (br. s., 3H), 2.01-2.43 (m, 4H), 1.72 (s, 3H), 1.42 (br. s., 6H).

Biological Data

Compounds of the invention may be tested for in vitro biological activity in accordance with the following assays:

Measurement of NK Binding Affinity

The NK1 binding affinity of the compounds of the invention was determined using the following filtration binding assay using [$^3$H]-GR205171 as radioligand for human NK1 receptor stably expressed in CHO (Chinese Hamster Ovary) cells (see C. Griffante et al, Br. J. Pharmacol. 2006, 148, 39-45; H. M. Sarau et al, J. Pharmacol. Experimental Therapeutics 2000, 295(1), 373-381 and D. T. Beattie et al., Br. J. Pharmacol. 1995, 116, 3149-3157).

CHO cells stably expressing the human cloned neurokinin NK1 receptor were cultured in Dulbecco's Modified Eagle's Medium/F12 Ham (DMEM/F12Ham) supplemented with 10% foetal bovine serum and 2 mM L-glutamine. Cells were maintained in 5% $CO_2$ in a humidified incubator at 37° C. Cells were harvested at confluency with PBS/EDTA (5 mM) and then pelleted by centrifugation (1000 g, 8 min, 4° C.). To prepare membranes, cell pellets were homogenised in 10 volumes of membrane preparation buffer and centrifuged (48,000 g, 20 min, 4° C.). The membranes were then re-suspended as 500 µL aliquots and stored at −80° C. until use.

Binding assay was carried out in 96 deep well polypropylene plates (Whatman) in a volume of 400 µl consisted of 100 µl of incubation buffer (containing 50 mM HEPES, pH 7.4, 3 mM $MnCl_2$, and 0.02% BSA), 4 µl of DMSO (total binding) or increasing concentrations of the compounds in the invention dissolved in DMSO (1 pM-1 µM final concentration), 100 µl of the radioligand [$^3$H]-GR205171 (0.2 nM final concentration) in incubation buffer and 200 µl of human NK1-CHO cell membranes suspension (4 µg/ml final) in incubation buffer. Non specific binding was defined by the addition of 1 µM unlabeled GR205171. The incubation proceeded at room temperature for 60 minutes. The reaction was stopped by rapid filtration through GF/C filterplates pre-soaked in 0.5% polyetylenimmine (PEI) followed by 3 washes with 1 ml ice cold 0.9% NaCl using a Cell Harvester (Perkin-Elmer). Filterplates were dried and retained radioactivity was counted in a Top Count (Perkin-Elmer).

Specific binding was determined by subtracting total binding from nonspecific binding, which was assessed as the binding in the presence of 1 µM GR205171. Percent inhibition of specific binding was determined for each concentration of the compounds of the invention and the $IC_{50}$, defined as the concentration required inhibiting 50% of the specific binding, obtained from concentration-response curves.

The affinity value was expressed as negative logarithm of the inhibition constant ($pK_i$) and was calculated from the $IC_{50}$ by the Cheng-Prusoff equation using the dissociation constant ($K_D$) of the radioligand and its concentration in the assay.

The compound of Example 11 was tested in five independent experiments and the average affinity value was pKi=9.88±0.07.

Measurement of NK Functional Potency:

Compounds of the invention were further characterised in a functional assay using FLIPR technology for the determination of their effect to inhibit the intracellular calcium release induced by interaction of NK receptors with its perspective ligands. Human U2OS cells transiently transduced with recombinant BacMam virus expressing human NK1, NK2 and NK3 receptors were used in the studies (see J. P. Condreay et al, Proc. Natl. Acad. Sci. USA 1999, 96(1): 127-132). Briefly, U2OS cells were harvested from tissue culture flasks, re-suspended to a cell density of 200-300K/ml and mixed with recombinant BacMam virus carrying NKR gene in a virus/cell ratio of 1% (v/v). 10K-15K cells/well were then seeded in 384-well Greiner bio-one plate in culture medium (DMEM with 10% FBS), incubated overnight in 5% $CO_2$ at 37° C. After aspirating the medium, cells were loaded 18-24 hr later with cytoplasmic calcium indicator Fluo-4 Calcium 3 dye (Molecular Devices Co.) in 30 uL/well buffer (Hank's balanced salts with 20 mM Hepes) and incubated in $CO_2$ at 37° C. for 60 minutes. 10uL/well assay buffer (Hank's balanced salts with 20 mM Hepes) containing different concentrations of compounds were then added to the cells for 30 minutes incubation at 37° C. Finally, 10 uL/well of NKR ligands in assay buffer containing 0.1% BSA was added to the cells and fluorescence signal read on a FLIPR system. Substance P, NKA and NKB peptides were used as tie ligands for NK1, NK2 and NK3 receptor, respectively. IC50 values of each compound were determined by an 11-point 3×-dilution inhibition curve. The potency each antagonist ($fpK_i$) was calculated from pIC50 by the Cheng-Prusoff equation using EC50 of ligand determined in a separate experiment. The compounds of Example 11, Examples 2, 4 and 6 were tested in the NK functional potency assay. The corresponding pKi values obtained as the average of at least two determinations are given in the following Table 2.

TABLE 2

| Example No. | $NK_1$ | $NK_2$ | $NK_3$ |
| --- | --- | --- | --- |
| Ex. 11 | 10.1 | <6.0 | 7.50 |
| Ex. 2 | >9.77 | 5.70 | 7.10 |
| Ex. 4 | >9.77 | 5.70 | 7.20 |
| Ex. 6 | >9.77 | 5.70 | 6.80 |

The ability of the compounds of the invention to penetrate the central nervous system and to bind at the $NK_1$ receptor may be determined using the gerbil foot tapping model as described by Rupniak & Williams, Eur. Jour. of Pharmacol., 1994.

Intracerebroventricular (icv) administration of the $NK_1$ receptor agonist GR73632 (R. M. Hagan et al., Neuropeptides 1991, 19 (2), 127-135) a characteristic hind leg foot tapping (GFT) response in gerbils which can be inhibited by potent $NK_1$ receptor antagonists. The gerbil foot tapping paradigm was carried out as follows; gerbils were dosed with compound of the invention, and following an appropriate pre-treatment time were anaesthetised using isofluorane/oxygen mixture. The skull was then exposed and 5 ul of GR73632 (3 pmol conc.) was injected by insertion of a cuffed 25 G needle to a depth of 4 mm below bregma, directly into the lateral ventricle (intracerebroventricular dosing). Immediately following the injection, gerbils were placed individually into a clear observation box to recover. Upon the gerbil regaining its righting reflex, the duration of repetitive hind foot tapping was recorded over a 5 minute period. The dose of the test compound required b inhibit by 50% the tapping induced by the NK1 agonist expressed as mg/kg is referred to as the $ID_{50}$ values.

GR73632-induced Foot Tapping behaviour was significantly attenuated by Example 11 at 0.3, 1.0 and 3.0 mg/kg p.o (P<0.01) with calculated $ID_{50}$ of approximately 0.2 mg/kg ($ID_{50}$ approximately 5 ng/ml plasma).

Compounds of the invention have also been found to demonstrate anxiolytic activity in validated preclinical tests. For example the marmoset human threat test (Costall et al., 1988

The study utilised in house laboratory-bred male and female common marmosets over 2 years of age, weighing 300-500 g. The animals were caged in couples, in a housing room maintained at 25±1° C., 60% humidity and a 12 hour light/dark cycle (lights on at 0600, with 30 min simulated dawn and twilight). Testing was carried out with the animals situated in the home cage.

One hour before the test animals were treated orally with vehicle (0.5% HPMC) or test compound (1 ml/kg). After a wash-out period of at least three days, treatments were reassigned and the study was complete when all animals had received all treatments. Number of specific behavioural postures in response to the human threat and the number of jumps were analysed in this study. The postures recorded in the test were those described by Costall et al (1988). and the number of jumps from the back of the cage to the cage front provided an index of locomotor activity to assess potential for sedation or locomotor stimulation.

Example 11 was administered at 0.1, 0.3 or 1 mg/kg according the procedure described above and the compound caused a dose dependent reduction in the number of postures performed by the animals which reached statistical significance at 0.3 and 1 mg/kg (*P<0.01). Results are reported in Table 3. This effect was not accompanied by a reduction in the number of jumps performed by the animals and as such is interpreted as an anxiolytic effect of the compound.

TABLE 3

| Treatment | Dosage mg/kg | No. postures | No. jumps |
|---|---|---|---|
| Vehicle |  | 11.0 ± 0.6 | 16.3 ± 1.7 |
| Ex. 11 | 0.1 | 9.4 ± 1.0 | 20.1 ± 2.1 |
| Ex. 11 | 0.3 | *6.3 ± 0.9 | 13.4 ± 2.5 |
| Ex. 11 | 1 | *4.0 ± 0.4 | 13.0 ± 2.1 |

Table 3 shows the results of Example 11 in the marmoset human threat test. Results are expressed as mean±SEM (n=7). of number of postures and as a mean±SEM (n=4) of number of jumps. Data were subjected to one-way analysis of variance (ANOVA) followed by Dunnett's test, comparing each compound dose with vehicle treatment, using Statistica software (version 8.0) Statistically significant differences with respect to vehicle are indicated as *P<0.01.

The invention claimed is:

1. A method for treatment of an inflammatory disease in mammals, which comprises administering to a sufferer a therapeutically effective amount of a compound of formula (I)

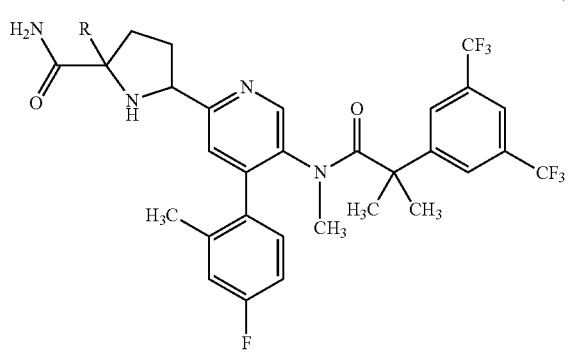

(I)

wherein R is $C_{1-4}$ alkyl, or a pharmaceutical acceptable salt thereof.

2. The method according to claim 1, wherein the inflammatory disease is a bladder inflammatory disease.

3. The method according to claim 2, wherein the bladder inflammatory disease is selected from cystitis, overactive bladder and urge incontinence.

4. The method according to claim 1, wherein the inflammatory disease is an eye inflammation.

5. The method according to claim 1, wherein the inflammatory disease is associated with asthma, influenza, chronic bronchitis and rheumatoid arthritis.

6. The method according to claim 1, wherein the inflammatory disease is a gastrointestinal tract inflammation.

7. The method according to claim 6, wherein the gastrointestinal tract inflammation is selected from Crohn's disease, ulcerative colitis, ulcerative colitis, inflammatory bowel disease and non-steroidal anti-inflammatory drug induced damage.

8. The method according to claim 1, wherein the inflammatory disease is a skin inflammatory diseases.

9. The method according to claim 1, wherein the skin inflammatory diseases is selected from herpes and eczema.

10. The method according to claim 1, wherein the inflammatory disease is a dental inflammation.

11. The method according to claim 1, wherein the said mammal is a human.

12. The method according to claim 1, wherein the compound of formula (I) is

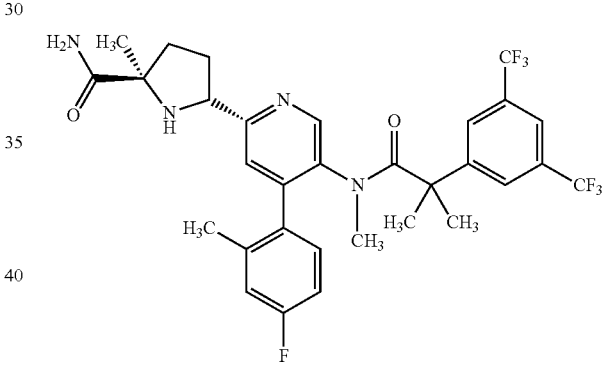

or a pharmaceutically acceptable salt thereof.

13. The method according to any of claim 1, wherein the compound of formula (I) is
(5R)-5-[5-[{2-[3,5-bis(trifluoromethyl)phenyl]-2-methyl-propanoyl}(methyl)amino]-4-(4-fluoro-2-methylphenyl)-2-pyridinyl]-2-methyl-D-prolinamide.

* * * * *